US008834367B2

(12) United States Patent
Laan et al.

(10) Patent No.: US 8,834,367 B2

(45) **Date of Patent: *Sep. 16, 2014**

(54) DEVICE AND METHOD FOR ASSESSING BLOOD GLUCOSE CONTROL

(71) Applicant: Roche Diagnostics Operations, Inc., Indianapolis, IN (US)

(72) Inventors: Remmert Laan, Weinheim (DE); Stefan Weinert, Pendleton, IN (US); Robin Wagner, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/658,156

(22) Filed: Oct. 23, 2012

(65) Prior Publication Data

US 2013/0110549 A1 May 2, 2013

Related U.S. Application Data

(63) Continuation of application No. 12/040,458, filed on Feb. 29, 2008, now Pat. No. 8,317,699.

(51) Int. Cl.

| | |
|---|---|
| ***G01N 33/52*** | (2006.01) |
| ***C12Q 1/54*** | (2006.01) |
| ***G01N 21/86*** | (2006.01) |
| ***G06Q 90/00*** | (2006.01) |
| ***G06F 19/00*** | (2011.01) |
| ***G06Q 50/24*** | (2012.01) |
| *A61B 5/145* | (2006.01) |

(52) U.S. Cl.

CPC .............. *G06Q 90/00* (2013.01); *G06F 19/322* (2013.01); *G06Q 50/24* (2013.01); *G06F 19/3456* (2013.01); *G06F 19/3487* (2013.01); *A61B 5/14532* (2013.01)

USPC .......................................................... 600/365

(58) Field of Classification Search

None

See application file for complete search history.

(56) References Cited

U.S. PATENT DOCUMENTS

| | | | |
|---|---|---|---|
| 5,188,563 | A | 2/1993 | Hanauer |
| 5,437,024 | A | 7/1995 | French |
| 6,551,276 | B1 | 4/2003 | Mann et al. |
| 6,554,798 | B1 | 4/2003 | Mann et al. |
| 6,872,200 | B2 | 3/2005 | Mann et al. |
| 6,936,029 | B2 | 8/2005 | Mann et al. |
| 6,979,326 | B2 | 12/2005 | Mann et al. |
| 6,997,920 | B2 | 2/2006 | Mann et al. |
| 7,008,378 | B2 | 3/2006 | Dean |

(Continued)

FOREIGN PATENT DOCUMENTS

| | | | |
|---|---|---|---|
| CN | 101010031 | A | 8/2007 |
| CN | 200953023 | Y | 9/2007 |
| EP | 0 800 082 | A2 | 10/1997 |

OTHER PUBLICATIONS

Accu-Check 360 by Roche, copyright date 2007.*

(Continued)

*Primary Examiner* — Anne Gussow
*Assistant Examiner* — Reza Ghafoorian
(74) *Attorney, Agent, or Firm* — Roche Diagnostics Operations, Inc.

(57) ABSTRACT

A blood glucose and lifestyle tracking apparatus is disclosed. The blood glucose and lifestyle tracking apparatus provides a method for recording both blood glucose values for fasting, postprandial, and preprandial time periods and lifestyle factors.

28 Claims, 18 Drawing Sheets

(56) References Cited

U.S. PATENT DOCUMENTS

| | | | |
|---|---|---|---|
| 7,025,743 | B2 | 4/2006 | Mann et al. |
| 7,219,455 | B1 | 5/2007 | Lee |
| 2005/0177397 | A1 | 8/2005 | Kane |
| 2007/0033074 | A1 | 2/2007 | Nitzan et al. |

OTHER PUBLICATIONS

Medtronic, "CGMS System Gold™: Continuous Monitoring System Overview", Nov. 1, 2007, 2 pgs., downloaded from http://www.minimed.com website.
Medtronic, "Value", Nov. 1, 2007, 2 pgs., downloaded from http://www.minimed.com website.
Medtronic, "Features", Nov. 1, 2007, 1 pg., downloaded from http://www.minimed.com website.
Medtronic, "Specifications", Nov. 1, 2007, 2 pgs., downloaded from http://www.minimed.com website.
Medtronic, "Indications", Nov. 1, 2007, 1 pg., downloaded from http://www.minimed.com website.
Medtronic, "Clinical References", Nov. 1, 2007, 12 pgs, downloaded from http://www.minimed.com website.
Medtronic, "Case Study", Nov. 1, 2007, 2 pgs., downloaded from http://www.minimed.com website.
Medtronic, "FAQ", Nov. 1, 2007, 6 pgs., downloaded from http://www.minimed.com website.
Decode Study Group, on behalf of the European Diabetes Epidemiology Group, "Glucose Tolerance and Cardiovascular Mortality: Comparison of Fasting and 2-Hour Diagnostic Criteria," Arch Intern Med, Feb. 12, 2001, p. 397-405, vol. 161, American Medical Associate.
De Marco, Roberto, MD et al., "Cause-Specific Mortality in Type 2 Diabetes: The Verona Diabetes Study," Diabetes Care, May 1999, pp. 756-761, vol. 22, No. 5.
Monnier, Louis, MD, et al. "Activation of Oxidative Stress by Acute Glucose Fluctuations Compared With Sustained Chronic Hyperglycemia in Patients With Type 2 Diabetes," Journal of the American Medical Associate, 2006, pp. 1681-1687, vol. 295, No. 14.
Chiasson, Jean-Louis, MD, et al., "Acarbose Treatment and the Risk of Cardiovascular Disease and Hypertension in Patients With Impaired Glucose Tolerance: The STOP-NIDDM Trial," Journal of the American Medical Association, Jul. 23/30, 2003, pp. 486-493, vol. 290, No. 4.
Esposito, Katherine, MD, et al., "Regression of Carotid Atherosclerosis by Control of Postprandial Hyperglycemia in Type 2 Diabetes Mellitus," American Heart Association Journal, 2004, pp. 214-219, American Heart Association, Inc.
Accu-Check 360 degree, copyright date 2007.
International Preliminary Search Report on Patentability for PCT/EP2009/001321 issued by the European Patent Office on Jul. 28, 2009 (7 pages).

* cited by examiner

| | | 104 | | | | | | 106 | |
|---|---|---|---|---|---|---|---|---|---|
| PATIENT NAME | | | | | | INSULIN NAME | | | |
| PATIENT PHONE | | | | 122 | | | | | |
| | | 128 | 130 | 132 | 134 | 136 | | 138 | 140 |
| | | Day 1 | | Date | | | | | |
| | | Before Breakfast | 2 hours after Breakfast | Before Lunch | 2 hours after Lunch | Before Dinner | | 2 hours after Dinner | Before Bed |
| | Time | | | | | | | | |
| | Meal Size S M L | - | S M L | - | S M L | - | | S M L | - |
| | Energy Level* | 1 2 3 4 5 | 1 2 3 4 5 | 1 2 3 4 5 | 1 2 3 4 5 | 1 2 3 4 5 | | 1 2 3 4 5 | 1 2 3 4 5 |
| | Blood Glucose | | | | | | | | |
| BLOOD GLUCOSE RANGE / TOO HIGH | >300 mg/dL | | | | | | | | |
| | 261-300 mg/dL | | | | | | | | |
| | 221-260 mg/dL | | | | | | | | |
| | 181-220 mg/dL | | | | | | | | |
| | 141-180 mg/dL | | | | | | | | |
| | 111-140 mg/dL** | | | | | | | | |
| | 81-110 mg/dL** | | | | | | | | |
| TOO LOW | 51-80 mg/dL | | | | | | | | |
| | <50 mg/dL | | | | | | | | |

| *ENERGY LEVEL | | | | | |
|---|---|---|---|---|---|
| What is your energy level? | 1 Very Low | 2 Somewhat Low | 3 Moderate | 4 Somewhat High | 5 Very High |

WARNING: Do not adjust your prescribed oral medication or insulin therapy without first consulting your physician.
**American College of Endocrinology Consensus Statement on Guidelines for Glycemic Control 2002

―176

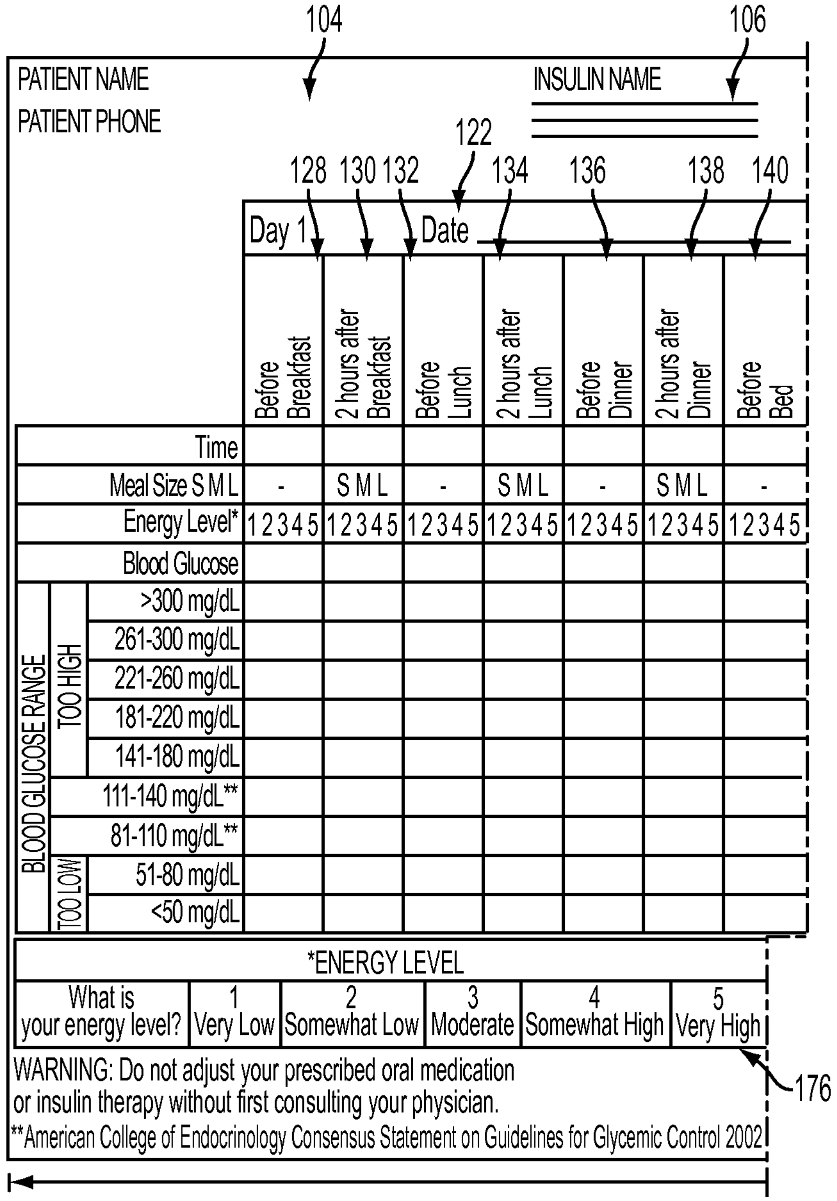

DEVICE AND METHOD FOR ASSESSING BLOOD GLUCOSE CONTROL

CROSS-REFERENCE TO RELATED APPLICATIONS

The present application is filed under 35 U.S.C. §111(a) as a continuation of U.S. application Ser. No. 12/040,458, filed on Feb. 29, 2008.

BACKGROUND AND SUMMARY OF THE INVENTION

The present invention relates generally to methods for assessing control of a health characteristic and in particular to methods for assessing control of blood glucose.

It is known that the ability of a patient to control their blood glucose impacts other characteristics of their health. It is known for patient's to take blood glucose readings with a blood glucose meter and to monitor their blood glucose levels. Several software programs are available which communicate with the blood glucose meter and provide reports for the patient and doctor to analyze their blood glucose levels. Many patients test randomly and infrequently and therefore their blood glucose values do not provide an accurate and complete (time series) picture of their glycemic control. Patients may bring to their physician's office a completed logbook with no visualization, a blood glucose meter on which the physician may scroll through values with no visualization, or a blood glucose meter whose values are downloaded to a software application which generates reports.

Many caregivers continue to monitor the blood glucose of a patient by periodically taking a blood sample and having an HbA1c test performed which provides an indication of the patient's average blood glucose level. Therapy decisions by the caregiver are then based in part on the results of the HbA1c test. This is especially true in the case of non-insulin type 2 patients. Further, the patient may make lifestyle decisions based in part on the results of the HbA1c test.

A patient's average blood glucose level does not always provide an adequate snapshot of a patient's glycemic control. As explained herein, by conducting episodic monitoring for a short period of time more informed therapy and/or lifestyle decisions may be made. This not only provides a better standard of care for the patient, but also reduces the likelihood of future complications and expenses; thereby causing the patient to hopefully have a better quality of life.

In a exemplary embodiment of the present disclosure, an apparatus for tracking blood glucose values and lifestyle factors is provided. The apparatus including: a substrate having a front side including a plurality of regions for tracking blood glucose values and a second side including a portion having a plurality of instructions for using the plurality of regions for tracking blood glucose values. The substrate being foldable such that the portion having the plurality of instructions on the second side overlap a portion of the front side.

In another exemplary embodiment of the present disclosure, an apparatus for tracking blood glucose values and lifestyle factors is provided. The apparatus including: a substrate having a front side including a plurality of regions for tracking blood glucose values. The plurality of regions including a first region for recording an actual blood glucose value and a second region for placing a graphical marker indicating a selection of a first range of a plurality of ranges of blood glucose values. The plurality of ranges including at least one range below a target range, at least one target range, and at least one range above a target range.

In a further exemplary embodiment of the present disclosure, a method of assessing blood glucose levels is provided. The method including the steps of: receiving a blood glucose form over a network, the blood glucose form including a plurality of indicia related to a plurality of blood glucose readings; storing a plurality of database records based on the plurality of indicia related to the plurality of blood glucose readings; and providing at least one report based on the plurality of database records, the at least one report graphically representing at least a portion of the plurality of indicia related to the plurality of blood glucose readings.

In yet a further exemplary embodiment of the present disclosure, a method of assessing blood glucose levels is provided. The method including the steps of: providing a patient with a prescription for test strips for a blood glucose meter and a blood glucose form; receiving the blood glucose form from the patient, the blood glucose form including a plurality of indicia related to a plurality of blood glucose readings of the blood glucose meter; and receiving at least one report based on the plurality of indicia related to the plurality of blood glucose readings.

In still another exemplary embodiment of the present disclosure, a system for tracking physiological information with a blood glucose meter is provided. The system including: a plurality of test strips for use with the blood glucose meter; and a blood glucose and lifestyle factors tracking apparatus for recording a plurality of blood glucose values determined by the blood glucose meter and corresponding lifestyle factors.

In yet another exemplary embodiment of the present disclosure, a method of assessing blood glucose levels is provided. The method including the steps of providing a patient with a blood glucose and lifestyle factors tracking apparatus and receiving the blood glucose form from the patient. The blood glucose and lifestyle factors tracking apparatus including a first region for recording blood glucose values for at least a first fasting time period, a first preprandial time period, and a first postprandial time period for multiple consecutive days. The blood glucose and lifestyle factors tracking apparatus further including a second region for graphically representing the blood glucose values recorded in the first region. The second region being placed so that a first graphical marker in the second region corresponding to a first blood glucose value in the first region are aligned. The blood glucose and lifestyle factors tracking apparatus further including a third region for recording at least one lifestyle factor for each blood glucose value, the third region being positioned above the first region. The received blood glucose form including a plurality of manually recorded blood glucose values, a manually drawn graphical representation of the plurality of manually recorded blood glucose values; and a plurality of manually recorded indicia for the at least one lifestyle factor for each manually recorded blood glucose value.

Additional features and advantages of the present invention will become apparent to those skilled in the art upon consideration of the following detailed description of illustrative embodiments exemplifying the best mode of carrying out the invention as presently perceived.

BRIEF DESCRIPTION OF THE DRAWINGS

The detailed description of the drawings particularly refers to the accompanying figures in which:

FIGS. 1A-1C are detail portions of FIG. 1.

DETAILED DESCRIPTION OF THE DRAWINGS

The embodiments of the invention described herein are not intended to be exhaustive or to limit the invention to the precise forms disclosed. Rather, the embodiments selected for description have been chosen to enable one skilled in the art to practice the invention.

Figure 1:
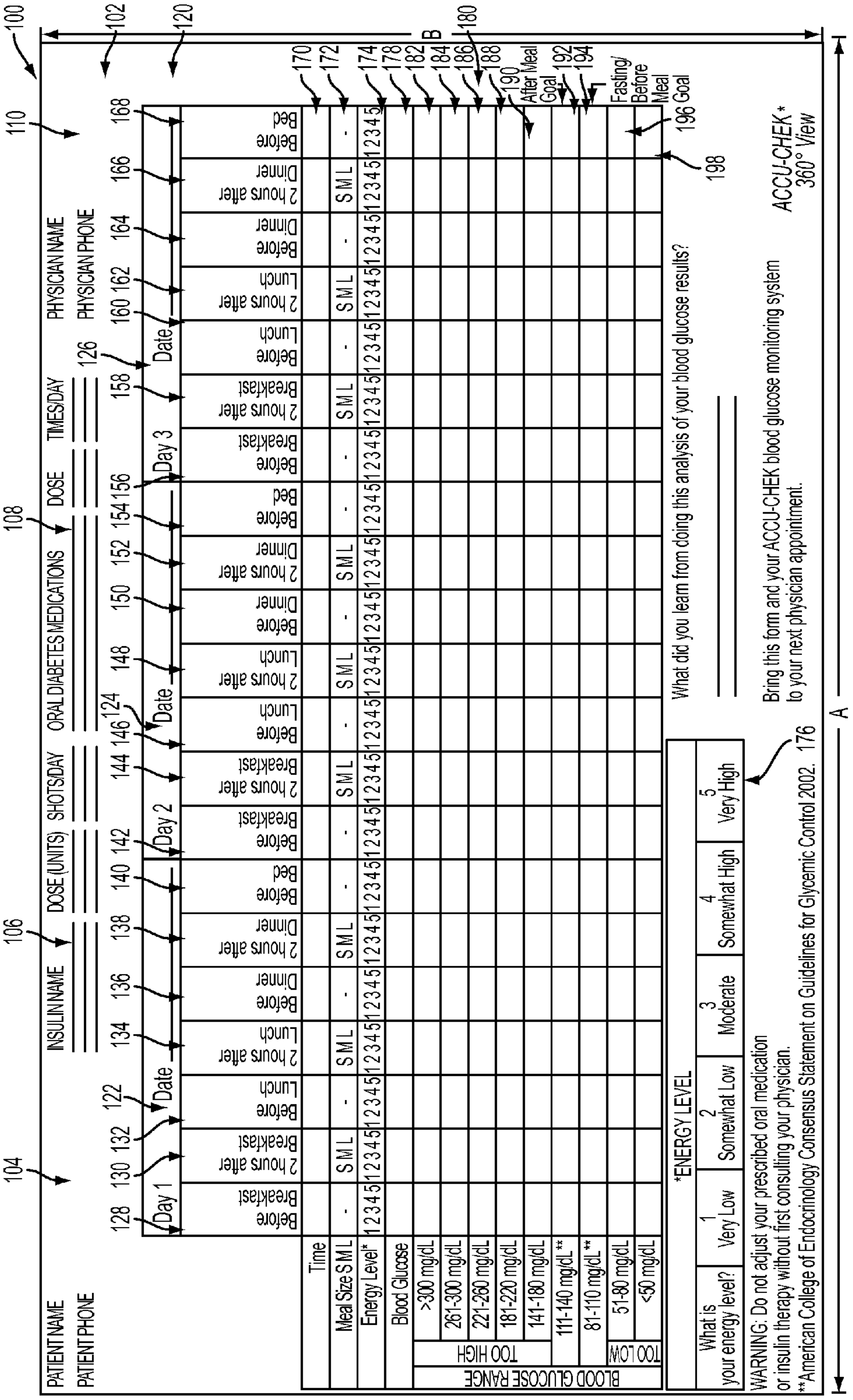
FIG. 1 is a front view of a blood glucose and lifestyle factors tracking apparatus.
Figure 1B:
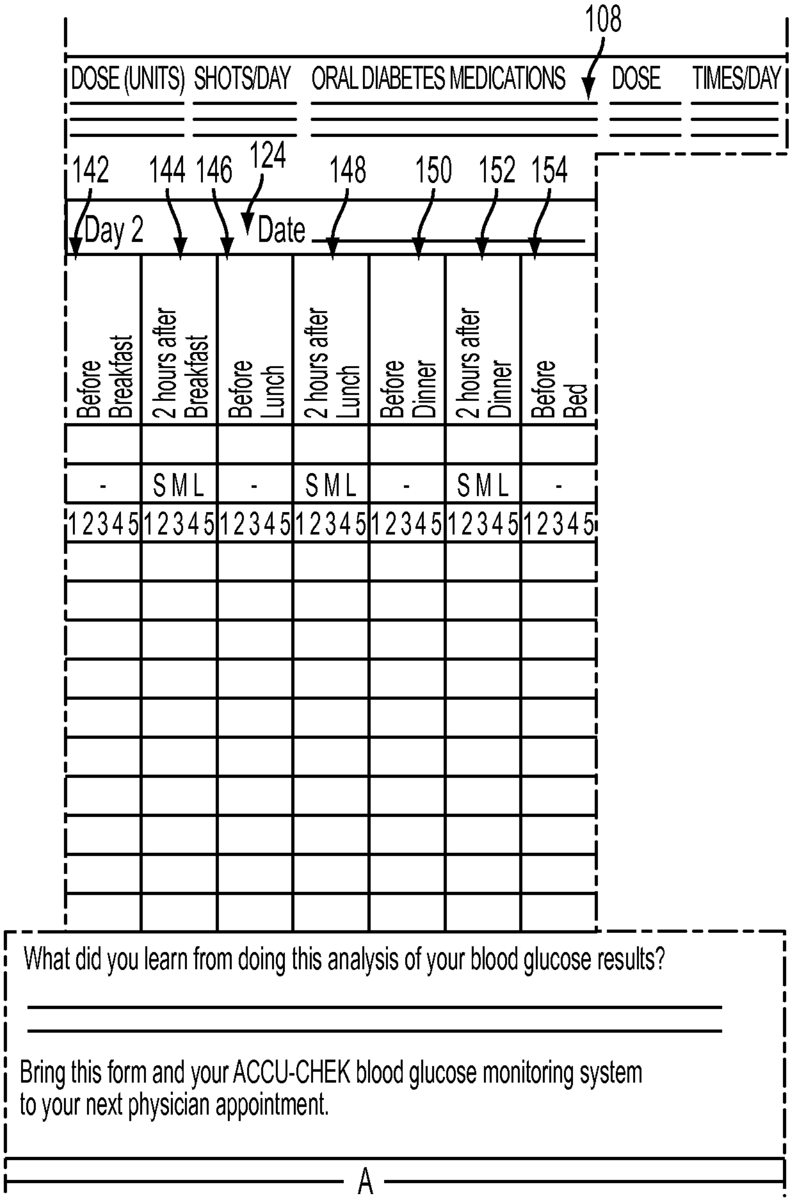
Figure 1C:
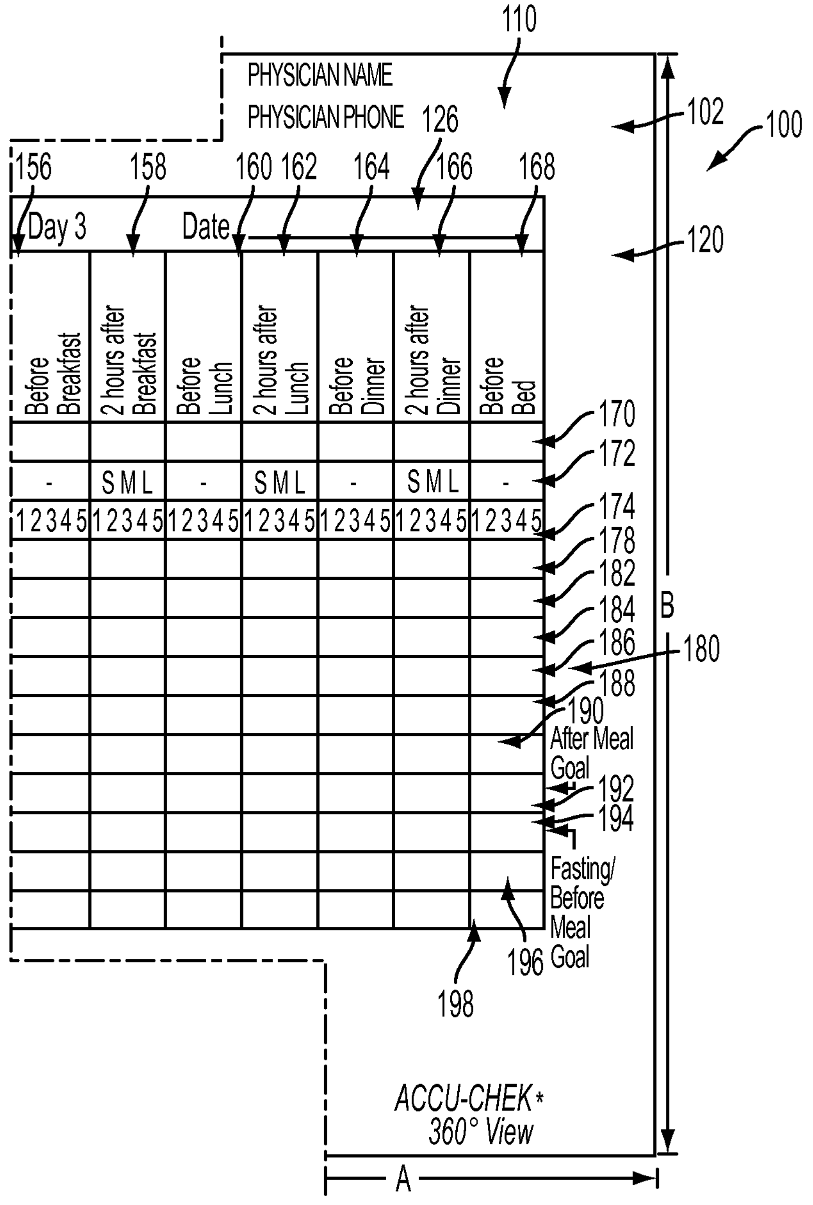

Referring to FIG. 1, a front view of a blood glucose and lifestyle factors tracking apparatus 100 is shown. In one embodiment, blood glucose and lifestyle factors tracking apparatus 100 is provided on a substrate, such as a piece of paper or other foldable material. Blood glucose and lifestyle factors tracking apparatus 100 provides a method for patients to track their blood glucose values and for caregivers to make a more informed decision in therapy decisions.

With blood glucose and lifestyle factors tracking apparatus 100 patients are asked to test their blood glucose for a short time with a structured pattern. The data is captured via the blood glucose and lifestyle factors tracking apparatus 100. Caregivers may use blood glucose and lifestyle factors tracking apparatus 100, alone, or in combination with HbA1c to evaluate if the current therapy is effective, and if not, to determine the best way to change the current therapy. The blood glucose and lifestyle factors tracking apparatus 100 assists a caregiver in seeing the whole blood glucose picture of a patient, such as a patient with non-insulin treated type 2 diabetes. The blood glucose and lifestyle factors tracking apparatus 100 also may be used with patients having type 1 diabetes. Blood glucose and lifestyle factors tracking apparatus 100 assists a caregiver to observe a patient's overall glycemic control as well as fasting, preprandial and postprandial values.

In one embodiment, a patient should complete blood glucose and lifestyle factors tracking apparatus 100 at least three to four times a year before a regularly scheduled visit with their physician. In one embodiment, the blood glucose and lifestyle factors tracking apparatus 100 may be used at any time to evaluate a patient's response to new medication, changes in lifestyle, stress or illness. The blood glucose and lifestyle factors tracking apparatus 100 may be used as a gateway to the consistent monitoring of blood glucose values with a blood glucose tracking software application.

Referring to FIG. 1, blood glucose and lifestyle factors tracking apparatus 100 includes a first region 102 for providing patient identification information 104, insulin dosage information 106, oral medications 108, and physician identification information 110. A second region 120 is provided for the recording of blood glucose values and lifestyle factors. Blood glucose and lifestyle factors tracking apparatus 100 provides for the tracking of blood glucose values and lifestyle factors for three consecutive days 122, 124, and 126. Although blood glucose and lifestyle factors tracking apparatus 100 provides for the tracking of blood glucose values and lifestyle factors for three days 122, 124, and 126, it should be understood that from two to more than three days may be tracked instead.

First day 122 includes seven time periods 128-140. In a similar manner second day 124 includes seven time periods 142-154 and third day 126 includes seven time periods 156-168. Although each day 122-126 includes seven time periods, less or more time periods may be used. The time periods include fasting time periods, preprandial time periods, and postprandial time periods. Exemplary time periods for each day are "Before breakfast" (time periods 128, 142, and 156), "2 hours after breakfast" (time periods 130, 144, and 158); "Before lunch" (time periods 132, 146, and 160); "2 hours after lunch" (time periods 134, 148, and 162); "Before dinner" (time periods 136, 150, and 164); "2 hours after dinner" (time periods 138, 152, and 166); and "Before bed" (time periods 140, 154, and 168).

Blood glucose and lifestyle factors tracking apparatus 100 further includes a row 170 for indicating an actual time that the blood glucose test is taken. Row 170 includes a plurality of boxes for recording an indication of the times.

Blood glucose and lifestyle factors tracking apparatus 100 includes a row 172 for indicating a lifestyle factor, namely an indication of the size of the meal eaten. Row 172 includes a plurality of boxes for recording an indication of the size of meal eaten. Three graduations are provided for meal size: small, medium, and large. A medium size meal is an average meal eaten by the person. The estimation of the meal size is subjective, so it is not possible to give an exact definition of small, medium and large food intake or to make a comparison between patients based on absolute volumes of food. It has been found that most people are consistent in their personal estimates of meal size over time. In addition, the fact that the patient has to think about the meal size makes him or her in most cases aware of the effect of food on self monitoring of blood glucose (SMBG) and his/her personal eating habits. The patient's blood glucose should always be measured before a meal or a scheduled meal. If the patient skips the meal he/she may either test two hours later anyway, or skip the test. A patient should use the Accu-Chek 360° View at times with a consistent, stable schedule, if possible.

Blood glucose and lifestyle factors tracking apparatus 100 includes a row 174 for indicating a lifestyle factor, namely an indication of an energy level of the person. Row 174 includes a plurality of boxes for recording an indication of the patient's energy level. Five graduations of energy level are provided: 1, 2, 3, 4, and 5. An explanation of the graduations is provided in region 176.

Blood glucose and lifestyle factors tracking apparatus 100 further includes a row 178 for indicating the actual measured blood glucose value for each time period. Row 178 includes a plurality of boxes for recording an indication of the blood glucose values. In one embodiment, the blood glucose values are measured with a blood glucose meter. Exemplary blood glucose meters include Accu-Chek Aviva and Accu-Chek Advantage, both available from Roche Diagnostics located in Indianapolis, Ind. In one embodiment, row 174 is positioned above row 178 so that the patient records their energy level prior to recording their blood glucose value. In this manner, the magnitude of the blood glucose value should not be focused on by the patient in choosing the corresponding energy level.

The patient is also to graph the measured blood glucose values in region 180. Region 180 includes a plurality of rows 182-198, each including a textual label indicating the range of blood glucose values corresponding to the respective row. Rows 182-192 correspond to various blood glucose values above the target ranges. Row 194 corresponds to the blood glucose range corresponding to an after meal (postprandial) target blood glucose. Row 196 corresponds to the blood glucose range corresponding to a before meal (preprandial) target blood glucose. Rows 196 and 198 correspond to various blood glucose values below the target ranges.

In one embodiment, the entire rows 194 and 196 of blood glucose and lifestyle factors tracking apparatus 100 have a visual indicator to indicate that they correspond to target ranges. In one embodiment, the visual indicator is a color differentiation from the remaining rows 182-190, 196, and 198. In one example, rows 194 and 196 are yellow. In one embodiment, one or more of the columns for each day 122-126 also include a visual indicator. In one example, columns 130, 144, and 158 are a first shade of blue, columns 134, 148, and 162 are a shade of purple, columns 138, 152, and 166 are a second shade of blue, and the remaining columns are white except that they are yellow in the areas overlapping rows 194 and 196. In a similar manner, columns 130, 134, 138, 144, 148, 152, 158, 162, and 166 also have a yellowish tint in the areas overlapping rows 194 and 196. The color scheme of blood glucose and lifestyle factors tracking apparatus 100 allows for: ease of analysis, pattern recognition for different times of the day, easy recognition of normal values, and faxing and scanning into electronic medical records. In one embodiment, the length A and width B of blood glucose and lifestyle factors tracking apparatus 100 is selected to correspond to the size paper used for physical medical records in the respective countries.

Figure 2:
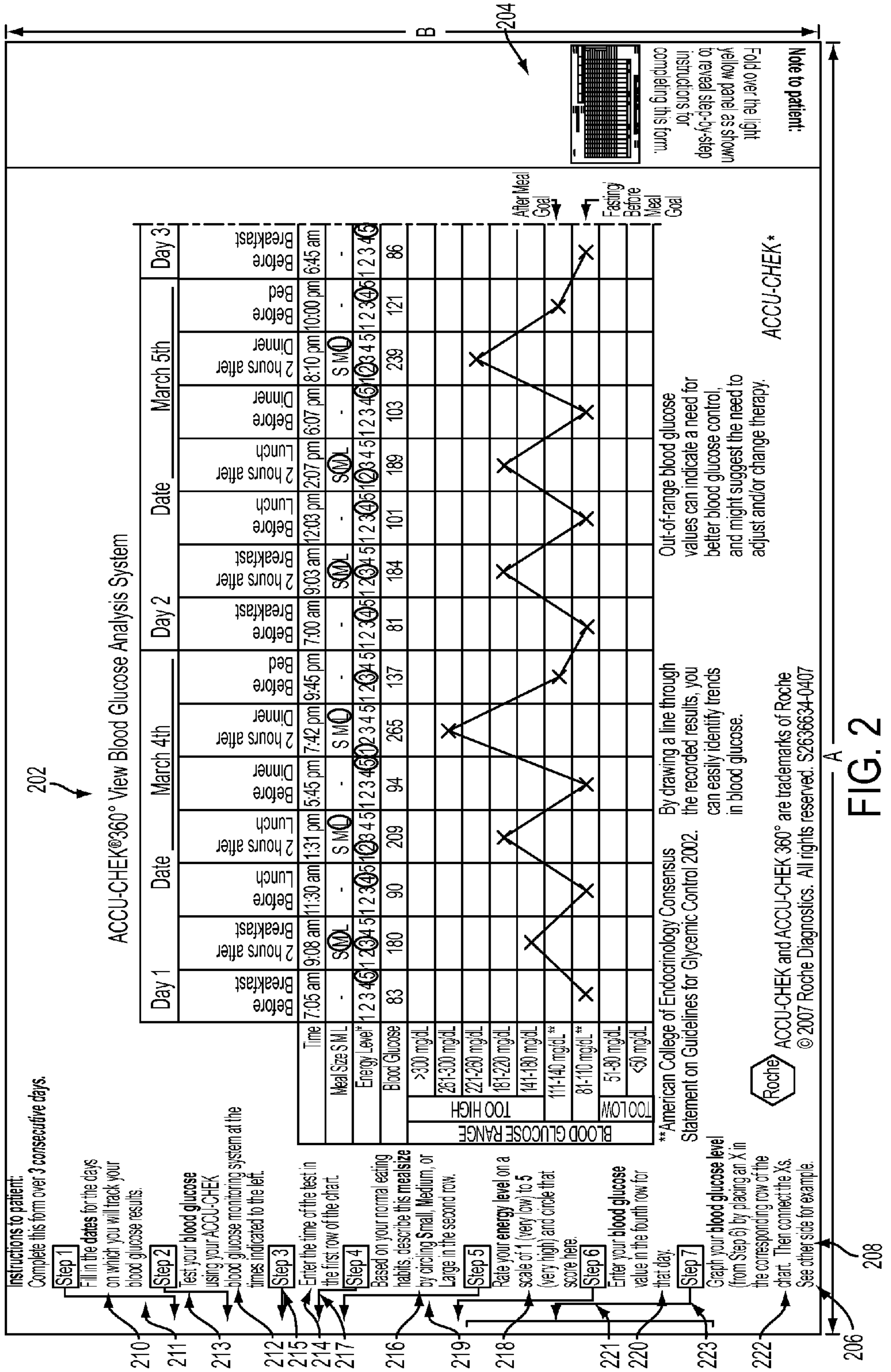
FIG. 2 is a back view of the blood glucose and lifestyle factors tracking apparatus of FIG. 1.
Figure 2A:
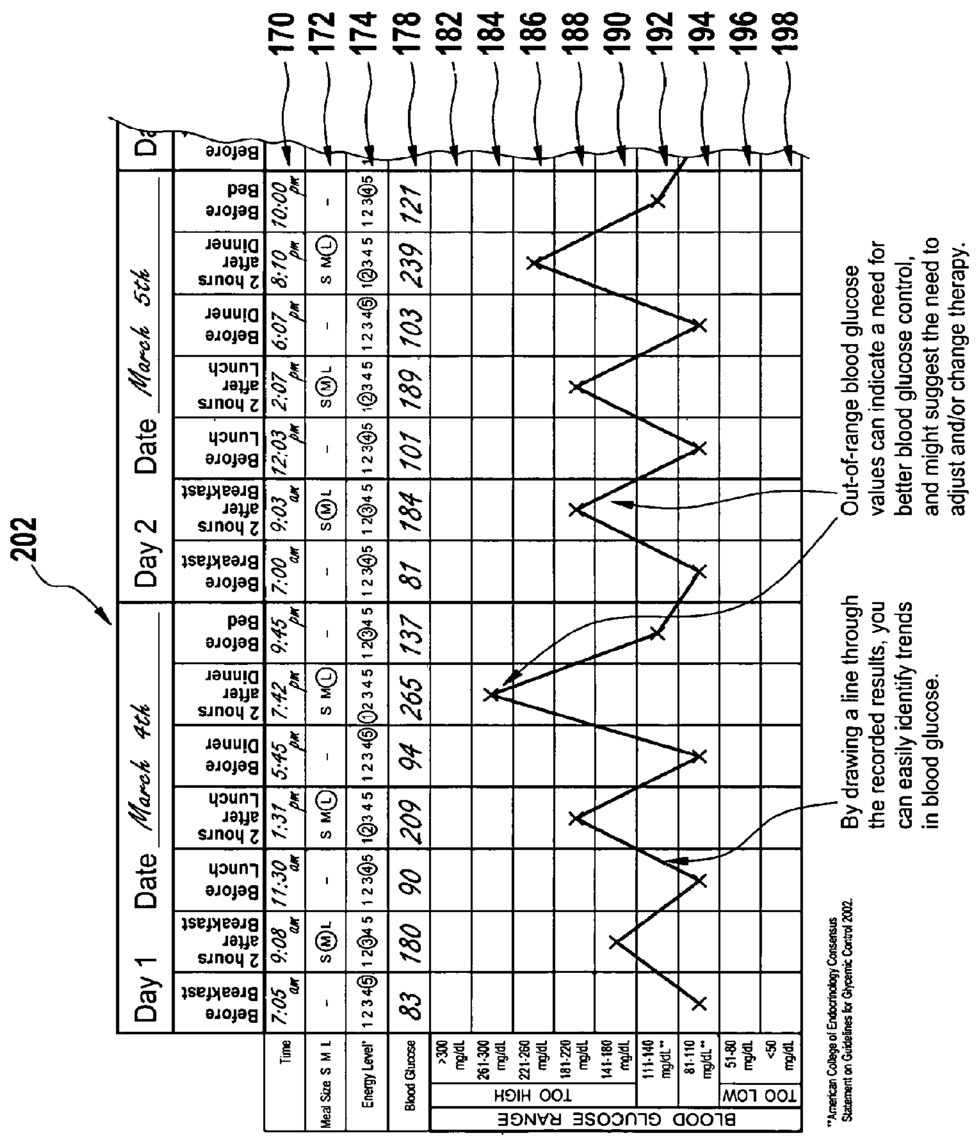
FIGS. 2A-2C are detail portions of FIG. 2.
Figure 2B:
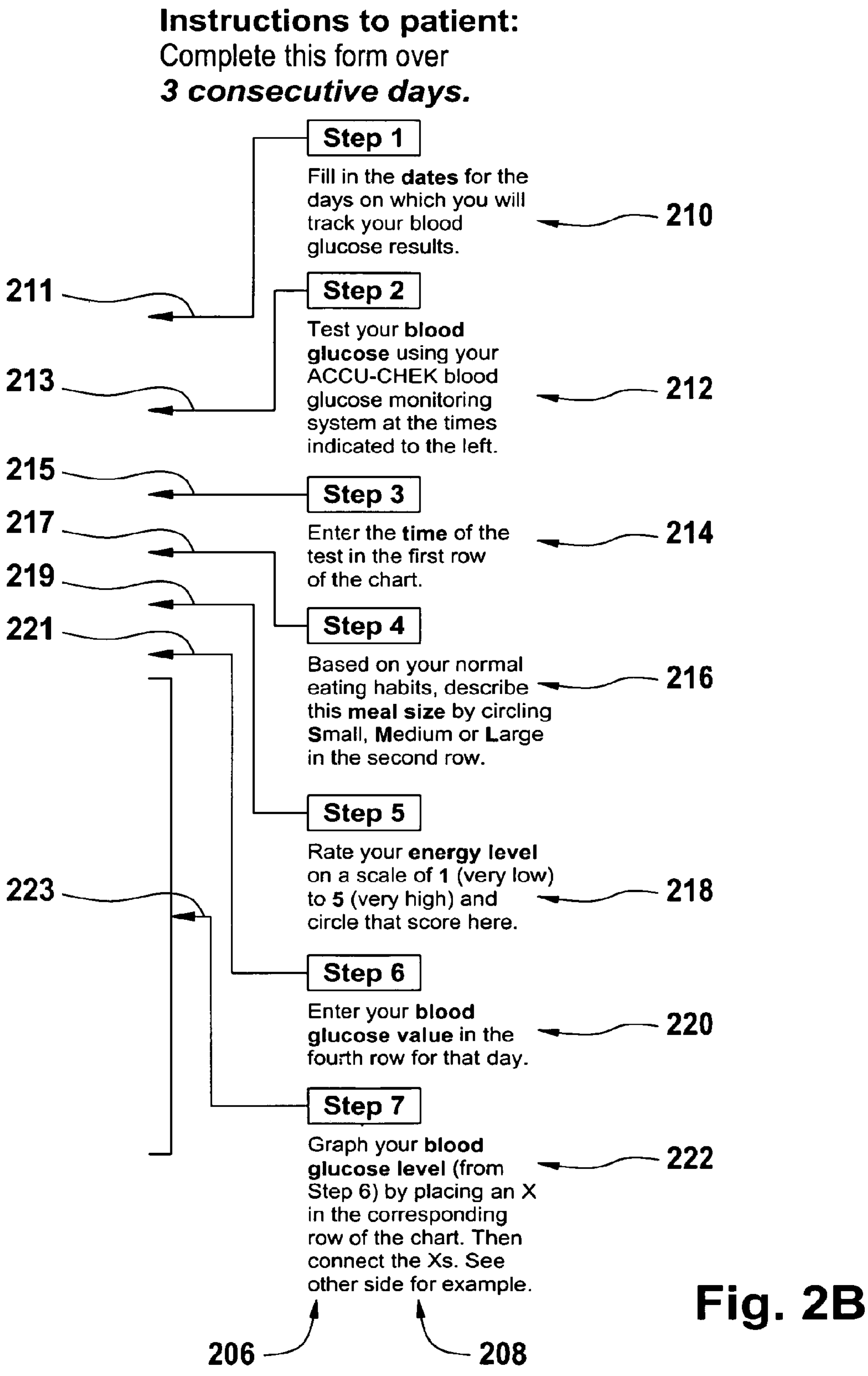
Figure 2C:
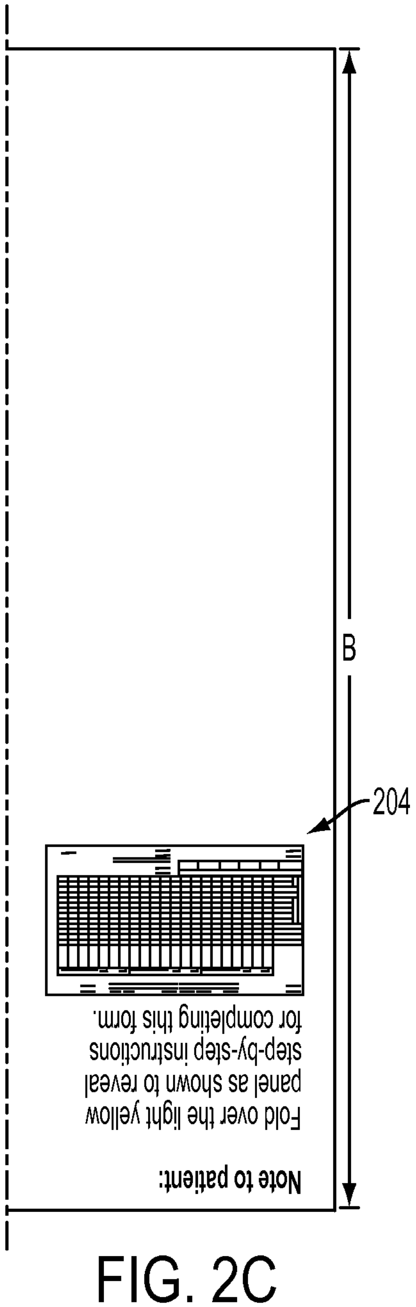
Figure 3:
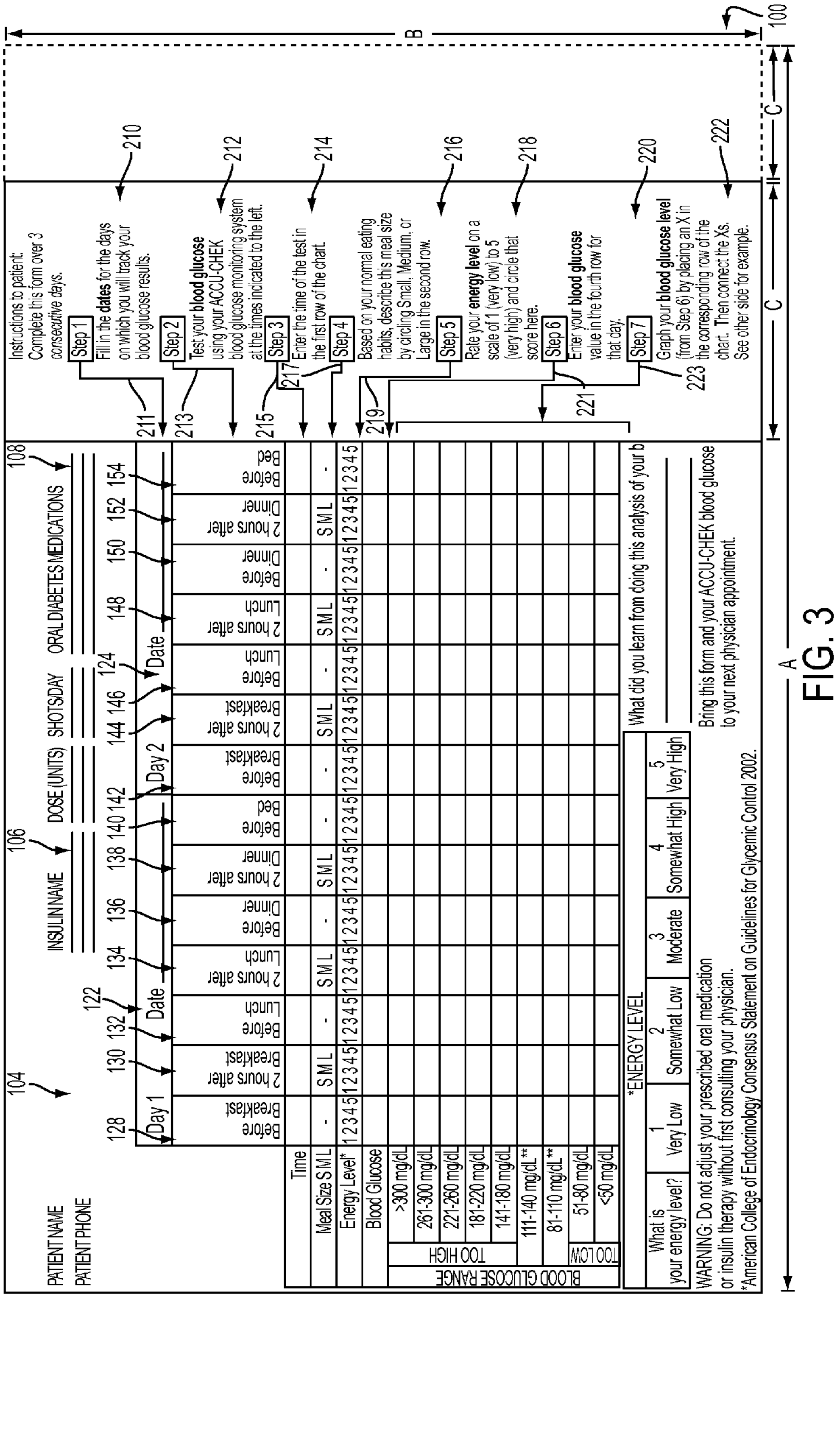
FIG. 3 is the front view of the blood glucose and lifestyle factors tracking apparatus of FIG. 1 with an instruction panel of the back side of the blood glucose and lifestyle factors tracking apparatus folded to overlap a portion of the front side of the blood glucose and lifestyle factors tracking apparatus.

Referring to FIG. 2, a back side of blood glucose and lifestyle factors tracking apparatus 100 includes an illustration of a completed front side of blood glucose and lifestyle factors tracking apparatus 100 in region 202. A detail view of a portion of region 202 is shown in FIG. 2A. Further, blood glucose and lifestyle factors tracking apparatus 100 includes a note to the user in region 204 on how to align a plurality of instructions 206 presented in region 208 with the front side of blood glucose and lifestyle factors tracking apparatus 100. As shown in FIGS. 1 and 2, blood glucose and lifestyle factors tracking apparatus 100 has a length A and a width B. Region 208 including plurality of instructions 206 has a length C. As shown in FIG. 3, by folding region 208 over a portion of the front side of blood glucose and lifestyle factors tracking apparatus 100 the plurality of instructions 206 in region 208 overlaps a portion of the front side of blood glucose and lifestyle factors tracking apparatus 100.

Plurality of instructions 206 illustratively include seven instructions 210-222. Instruction 210 instructs the user to fill in the dates for the days on which the patient will track his/her blood glucose values indicated by arrow 211. Instruction 212 instructs the user to perform the blood glucose tests in the time periods indicated by arrow 213. Instruction 214 instructs the user to provide the time for the blood glucose tests in row 170 as indicated by arrow 215. Instruction 216 instructs the user to, based on his/her normal eating habits, describe the meal size in row 172 as indicated by arrow 217. Instruction 218 instructs the user to provide an indication of his/her energy level in row 174 as indicated by arrow 219. Instruction 220 instructs the user to provide his/her blood glucose value in row 178 as indicated by arrow 221. Instruction 222 instructs the user to place an "X" in the row corresponding to the measured blood glucose and to connect the "X's" together as indicated by arrow 223.

The completed blood glucose and lifestyle factors tracking apparatus 100 is taken to the caregiver. Exemplary caregivers include a physician, a pharmacist or a diabetes nurse. The caregiver and the patient discuss the results of the three-day profile conducted with blood glucose and lifestyle factors tracking apparatus 100 and then decide what actions to take based on the results. The caregiver uses the self-monitoring data of the blood glucose and lifestyle factors tracking apparatus 100 and other information, such as HbA1c (if available), to decide if the current therapy is effective, and if not, to determine a change in the therapy. Caregivers often make decisions on treatment of patients with non-insulin treated type 2 diabetes solely based on HbA1c which is a valuable factor for the assessment of long-term glycemic control. But HbA1c does not tell the caregiver anything about short-term fluctuations of blood glucose levels which could lead to macrovascular complications.

It is well known that cardiovascular disease is the leading cause of death in patients with type 2 diabetes. Cardiovascular disease accounts for about forty percent of all deaths in diabetic patients. Blood glucose levels in all persons, including diabetes patients, are subject to temporal variations, called glycemic variability.

The connection between risk for cardiovascular disease and glycemic variability has been demonstrated in several studies. Wide glucose fluctuations, independent of mean glucose, are highly correlated with macrovascular complications in patients with type 2 diabetes. An important surrogate marker for glycemic variability is a patient's postprandial blood glucose levels. One study confirms the postprandial blood glucose levels as an independent risk factor for macrovascular complications: an increase of postprandial blood glucose levels of 1 mmol/l (approximately 18 mg/dl) leads to a mean increase of mortality of 8%. Recent research suggests that glucose fluctuations during postprandial periods and, more generally, during glucose swings, exhibit a more specific triggering effect on oxidative stress than chronic sustained hyperglycaemia. Thus, one of the mechanisms by which diabetes causes cardiovascular complications may be oxidative stress due to glucose variability.

Another investigation showed that atherosclerotic plaques may diminish if postprandial hyperglycemia is reduced. A further investigation showed a relative risk reduction for the development of cardiovascular events (nearly 50%) and in the development of new cases of hypertension (34%) in patients whose postprandial hyperglycemic values could be reduced. In addition, patients by understanding the connection to heart disease are more likely to monitor their blood glucose values than the traditional complications with diabetes, namely amputation and blindness.

Figure 4A:
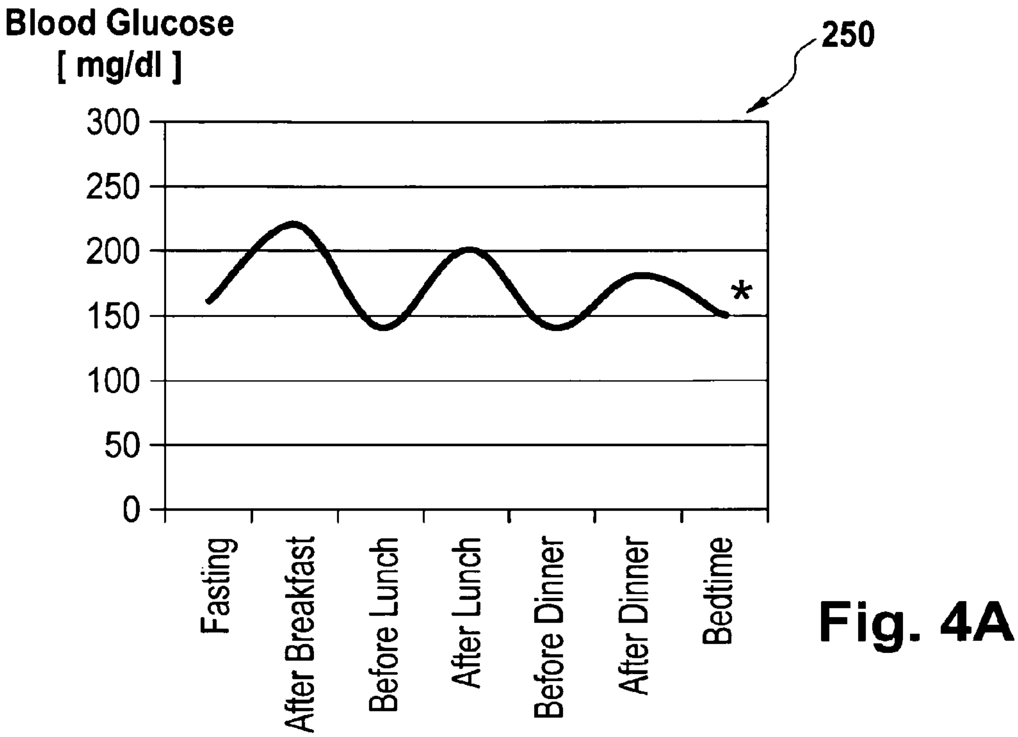
FIGS. 4A and 4B illustrate the glycemic variability for a first patient and a second patient, respectively.
Figure 4B:
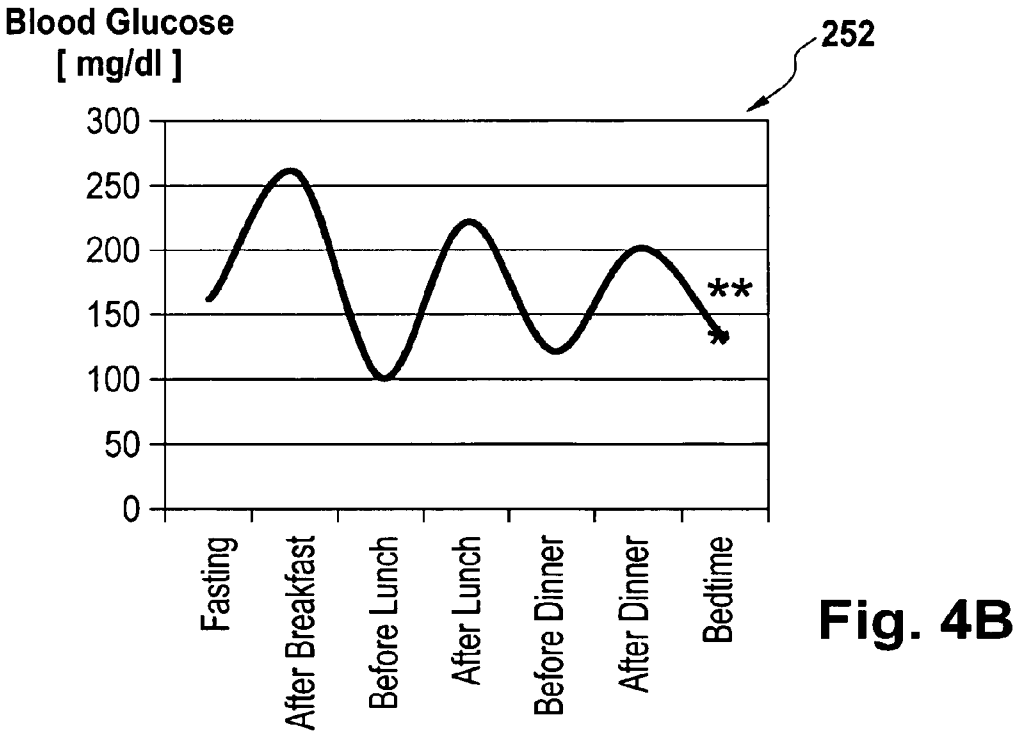

Referring to FIGS. 4A and 4B, the glycemic variability of a first patient, graph 250, and a second patient, graph 252, are shown. The second patient has a much higher glycemic variability than the first patent and is at a higher risk for macrovascular complications. However, a caregiver relying on HbA1c alone would not detect this difference between the first patient and the second patient. In fact, both the first patient and the second patient have generally the same HbA1c of 7.0% which equates to a mean blood glucose level of 170 mg/dl. (9.5 mmol/l). The treatment strategy for the first patient and the second patient may be different based on glycemic variability. For patient A the focus may be on reducing the fasting glucose first. For patient B the focus may also be on reducing the postprandial glucose.

The blood glucose and lifestyle factors tracking apparatus 100 is designed to monitor patients' glycemic variability in a simple, visual way to help achieve the goal of controlling glycemic variability. The blood glucose and lifestyle factors tracking apparatus 100 assists the caregiver to visualize overall glycemic control as well as fasting, preprandial and postprandial values. Four case studies are presented in FIGS. 5-8 to illustrate the use of blood glucose and lifestyle factors tracking apparatus 100.

Figure 5:
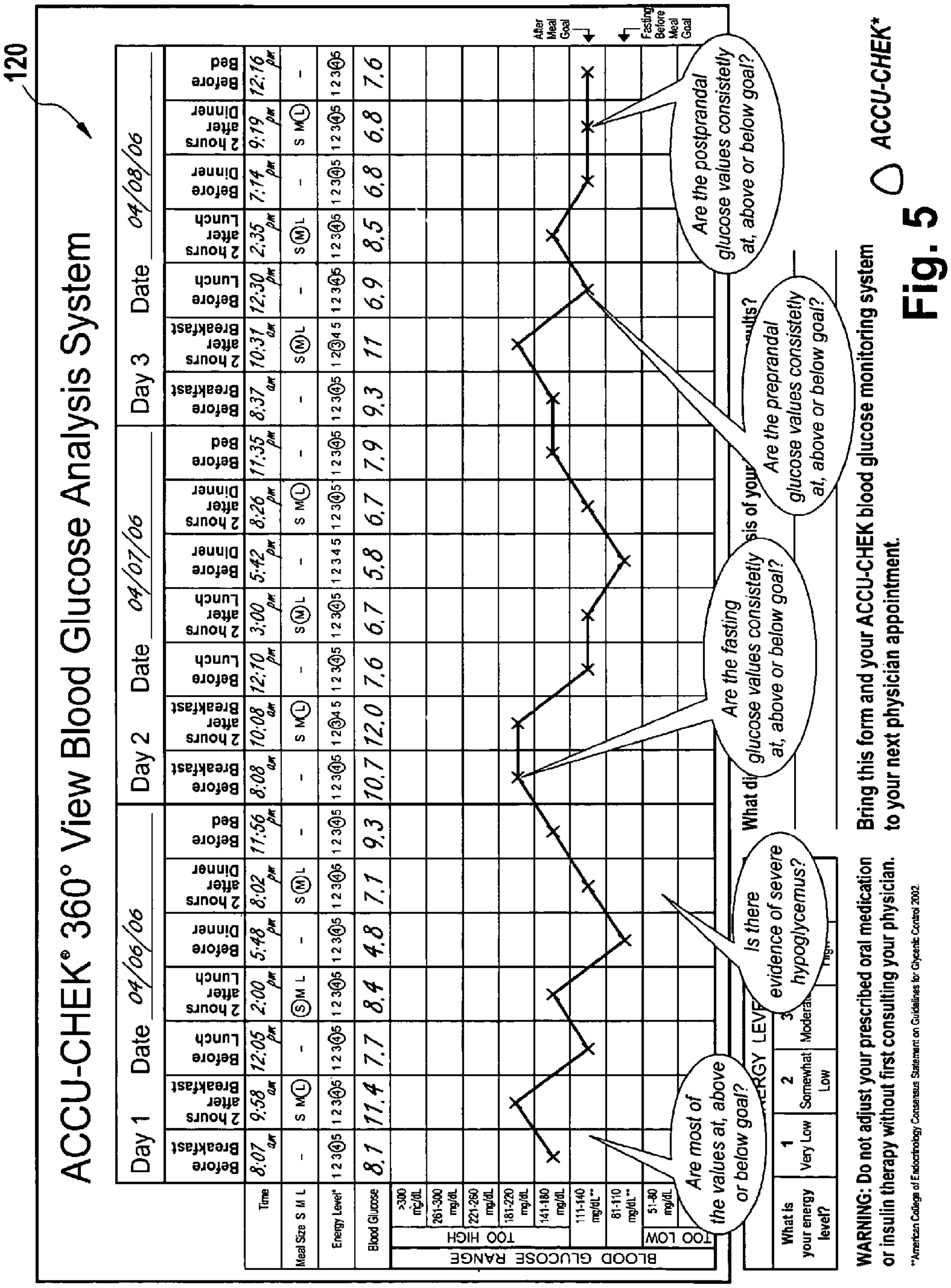
FIG. 5 illustrates a completed blood glucose and lifestyle factors tracking apparatus for a first case study.

Referring to FIG. 5, a completed blood glucose and lifestyle factors tracking apparatus 100 for a first patient named Beth is shown. Beth is a 72 year old Caucasian who has type 2 diabetes for 21 years. She is currently taking metformin 500 mg twice a day and Amaryl 4 mg with breakfast. She has raisin toast with coffee for breakfast. Her HbA1c1 is 6.8%.

A caregiver may consider the following questions when looking at the results depicted by blood glucose and lifestyle factors tracking apparatus 100. First, are most of the values at, above or below goal? Second, is there evidence of hypoglycemia? Third, are the fasting glucose values (i.e. before breakfast) consistently at, above or below goal? Fourth, are the preprandial glucose values (i.e. before meal) consistently at, above or below goal? Fifth, are the postprandial glucose values (i.e. after meal) consistently at, above or below goal? A caregiver may also consider the glycemic variability of Beth by considering from blood glucose and lifestyle factors tracking apparatus 100: Are postprandial values consistently >100 mg/dl (5.5 mmol/l) higher than preprandial values?

Referring to Table I, the answers to these inquiries are provided from an analysis of Beth's blood glucose and lifestyle factors tracking apparatus 100 along with some potential changes to therapy and/or lifestyle.

TABLE I

| Glycemic control factors | At, above or below goal | Possible actions |
|---|---|---|
| $HbA_{1c}$ at or below target of ≤6.5%? | Slightly above target | Education, lifestyle changes and possible medication adjustment or change |
| Are most of the values at, above or below goal? | Mostly above goal | Education, lifestyle changes and possible medication adjustment or change |
| Is there evidence of hypoglycemia? | No | |
| Are the fasting glucose values consistently at, above or below goal? | Above goal | Education, lifestyle changes and possible medication adjustment or change |
| Are the preprandial glucose values consistently at, above or below goal? | Mostly above goal | Education, lifestyle changes and possible medication adjustment or change |
| Are the postprandial glucose values consistently at, above or below goal? | Frequently above goal | Learn how food affects SMBG values, education, lifestyle changes and evaluation of medication |
| Glycemic variability: Are postprandial values consistently >100 mg/dl (5.5 mmol/l) higher than preprandial values? | No (Indication that glycemic variability is probably ok) | |

Figure 6:
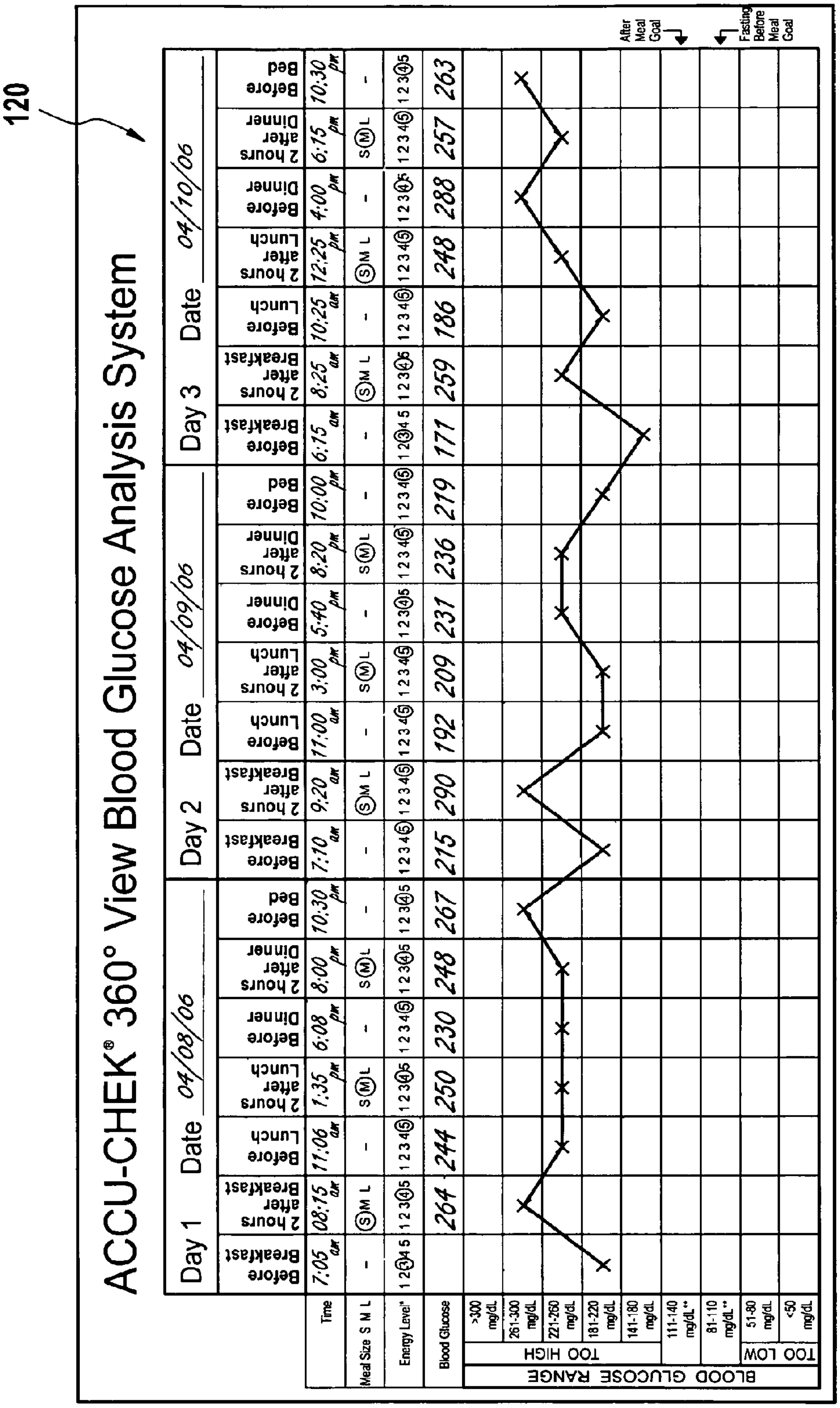
FIG. 6 illustrates a completed blood glucose and lifestyle factors tracking apparatus for a first case study.

Referring to FIG. 6, a completed blood glucose and lifestyle factors tracking apparatus 100 for a second patient named George is shown. George is a 76 year old male African American who has had type 2 diabetes for 2 years. He is currently taken pioglitazone 45 mg with breakfast and metformin 500 mg four times a day. His HbA1c today is 12.7%

Referring to Table II, the answers to the above inquiries are provided from an analysis of George's blood glucose and lifestyle factors tracking apparatus 100 along with some potential changes to therapy and/or lifestyle.

TABLE II

| Glycemic control factors | At, above or below goal | Possible actions |
|---|---|---|
| $HbA_{1c}$ at or below target of ≤6.5%? | No, far above target | Education, lifestyle changes and possible medication adjustment or change; encourage patient to stick with dietary changes he is already making |
| Are most of the values at, above or below goal? | Consistently above goal | Education, lifestyle changes and possible medication adjustment or change |
| Is there evidence of hypoglycemia? | No | |
| Are the fasting glucose values consistently at, above or below goal? | Consistently above goal | Education, lifestyle changes and possible medication adjustment or change; consider adding basal insulin |
| Are the preprandial glucose values consistently at, above or below goal? | Consistently above goal | Consider treating fasting hyperglycemia first; re-check pre- and post-prandial values after fasting |
| Are the postprandial glucose values consistently at, above or below goal? | Consistently above goal | Learn how food affects SMBG values; consider consulting with dietician; consider adding incretin agent or preprandial insulin |
| Glycemic variability: Are postprandial values consistently >100 mg/dl (5.5 mol/l) higher than preprandial values? | | Reassess after fasting hyperglycemia is addressed |

Figure 7:
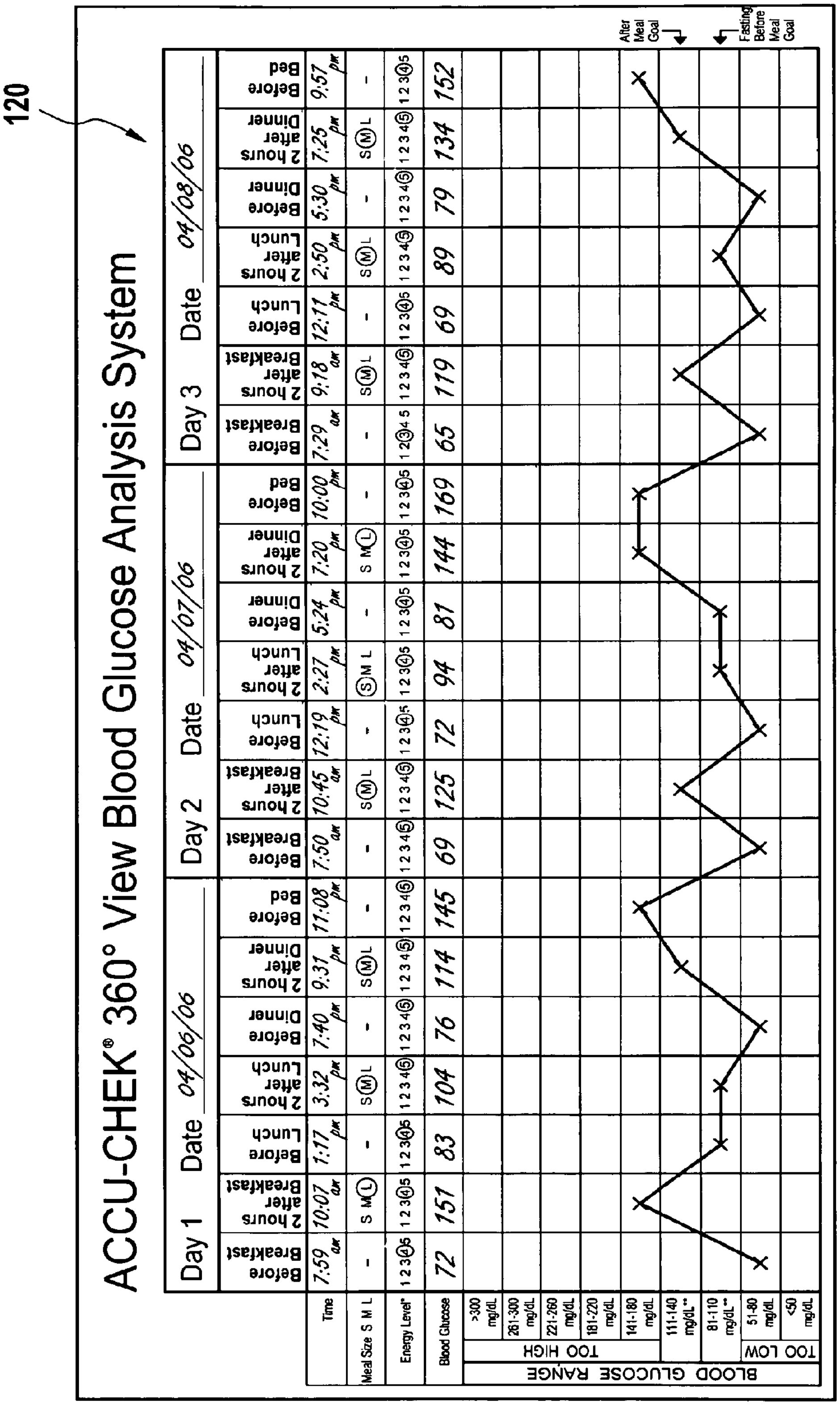
FIG. 7 illustrates a completed blood glucose and lifestyle factors tracking apparatus for a first case study.

Referring to FIG. 7, a completed blood glucose and lifestyle factors tracking apparatus 100 for a third patient named Maria is shown. Maria has significant hypoglycemic events. Maria is a 86 year old female Caucasian who has had type 2 diabetes for 5 years. She is currently taking glipizide 5 mg with breakfast and before bed. She feels weak and shaky before meals and feels a lot better after she has eaten. Her HbA1c today is 5.9%.

Referring to Table III, the answers to the above inquiries are provided from an analysis of Maria's blood glucose and lifestyle factors tracking apparatus 100 along with some potential changes to therapy and/or lifestyle.

TABLE III

| Glycemic control factors | At, above or below goal | Possible actions |
|---|---|---|
| $HbA_{1c}$ at or below target of ≤6.5% [1]? | Within target | Within normal range but patient complains of symptoms that may be consistent with hypoglycemia |
| Are most of the values at, above or below goal? | Mostly below goal | Consider reducing dose of current medication and frequency of administration |
| Is there evidence of hypoglycemia? | Yes, especially | Consider reducing dose of current medication and |

TABLE III-continued

| Glycemic control factors | At, above or below goal | Possible actions |
|---|---|---|
| | before meals | frequency of administration |
| Are the fasting glucose values consistently at, above or below goal? | Consistently below goal | Consider reducing dose of current medication and frequency of administration |
| Are the preprandial glucose values consistently at, above or below goal? | Frequently below goal | Resolve hypoglycemia and re-evaluate. |
| Are the postprandial glucose values consistently at, above or below goal? | Mostly at goal | Resolve hypoglycemia and re-evaluate; learn how food affects SMBG values |
| Glycemic variability: Are postprandial values consistently >100 mg/dl (5.5 mmol/l) higher than preprandial values? | | Re-assess after hypoglycemia is addressed. |

Figure 8:
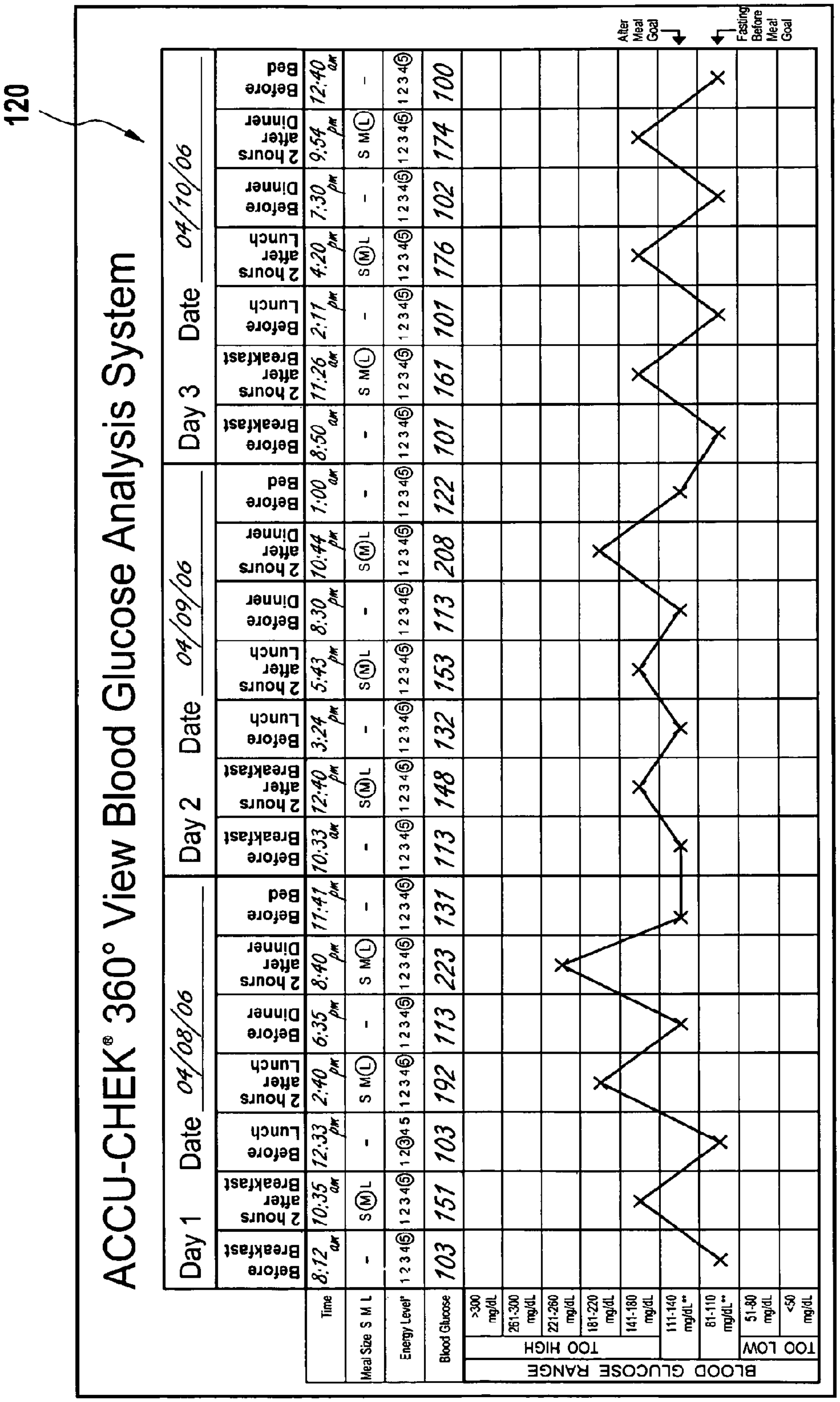
FIG. 8 illustrates a completed blood glucose and lifestyle factors tracking apparatus for a first case study.

Referring to FIG. 8, a completed blood glucose and lifestyle factors tracking apparatus 100 for a fourth patient named Giovanni is shown. Giovanni consistently shows postprandial hyperglycemia. Giovanni Bellinin is a 69 year old male Caucasian who has had type 2 diabetes for 2 years. He is currently taking glimepiride 1 mg with breakfast. He has recently discovered that he feels better if he eats smaller, more frequent meals. His HbA1c is 7.5%

Referring to Table IV, the answers to the above inquiries are provided from an analysis of Giovanni's blood glucose and lifestyle factors tracking apparatus 100 along with some potential changes to therapy and/or lifestyle.

TABLE IV

| Glycemic control factors | At, above or below goal | Possible actions |
|---|---|---|
| $HbA_{1c}$ at or below target of < 6.5% [1]? | Above target | Examine SMBG data to determine best options for adjusting therapy |
| Are most of the values at, above or below goal? | Mostly above goal | Education, lifestyle changes |
| Is there evidence of hypoglycemia? | No | |
| Are the fasting glucose values consistently at, above or below goal? | Most (⅔) fasting values are at goal | |
| Are the preprandial glucose values consistently at, above or below goal? | Some are at goal but some are above | |
| Are the postprandial glucose values consistently at, above or below goal? | Consistently above goal | Learn how food affects SMBG values, consider medication adjustment or change; consider incretin agents for post-prandial control |
| Glycemic variability: Are postprandial values consistently >100 mg/dl (5.5 mmol/l) higher than preprandial values? | Possibly higher than desirable with large post-prandial excursions | Re-assess after treating postprandial hyperglycemia |

Figure 9:
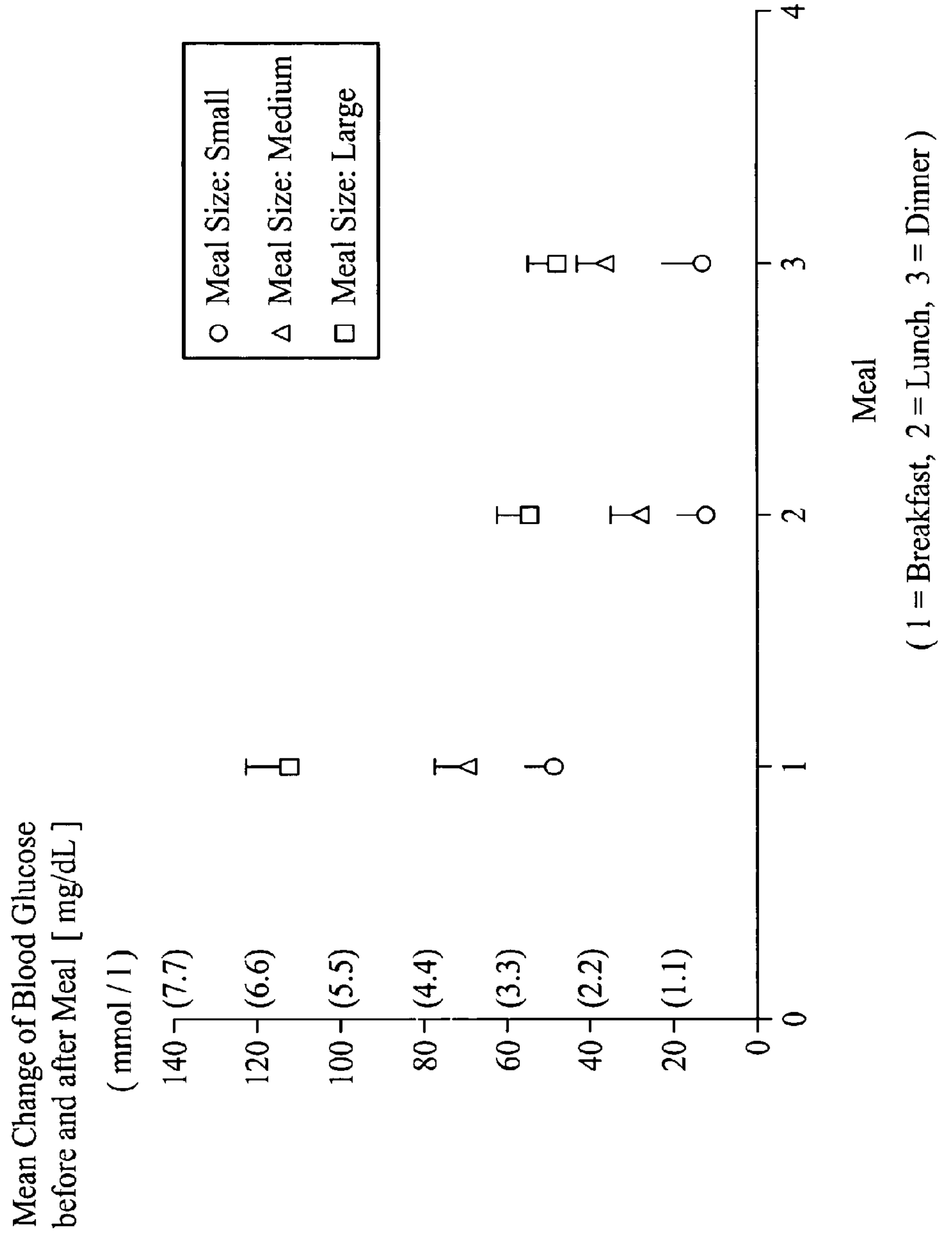
FIG. 9 illustrates the mean change of blood glucose before and after a meal for a population based on meal size.

The use of blood glucose and lifestyle factors tracking apparatus 100 not only provides a look at the blood glucose values, but also ties those values to lifestyle factors, namely meal size and energy level. Referring to FIG. 9, the mean change in blood glucose value from preprandial to two-hours postprandial for thirty subjects with diabetes having a mean age of sixty-six years and a mean duration of diabetes of 9.6 years are provided. The group had a mean HbA1c of 8.0%.

Based on HbAc1 alone, this group of subjects would be considered by many primary care physicians to have decent control and not warrant a therapy change. However, as an analysis of data derived from the completed blood glucose and lifestyle factors tracking apparatus 100 for the patients, this group of patients have significant postprandial excursions in the morning due partly to increased insulin resistance and partly to meal size. The glycemic variability is considerably less at lunch and dinner but still significant for those eating large meals.

The effectiveness of episodic monitoring of blood glucose on improving patient care was studied in a study presented as a poster at the European Association for the Study of Diabetes in September 2007 titled "Primary Care Physicians Identify and Act on Glycemic Abnormalities Found in Episodic, Intensive Blood Glucose Monitoring Data from Non-Insulin Treated Type 2 Diabetics." As stated herein, primary care physicians often make therapy adjustments for non-insulin treated type 2 diabetics on the basis of HbA1c alone without considering self-monitoring blood glucose (SMBG) data. The purpose of this study was to determine if primary care physicians could accurately identify glycemic abnormalities in episodic (short term), intensive SMBG data from non-insulin treated type 2 diabetics and if their therapeutic decisions would be changed by evaluation of SMBG data.

In the study twenty-three case studies demonstrating a range of glycemic states were prepared from data obtained from subjects with type 2 diabetics who participated in a prior clinical trial on episodic, intensive SMBG. Case studies included patients' history, current medications, current HbA1c values, and 3-7 days of SMBG data. Five diabetes care experts evaluated the case studies, identified glycemic abnormalities, and determined if and how the patients' therapy should be changed. Subsequently, board certified family practitioners and internists evaluated the case studies first without SMBG data and then with SMBG data. Their interpretations of the SMBG data were compared to the interpretations of the experts. The primary care physicians' therapeutic recommendations for case studies without SMBG data were compared to those the primary care physicians made for case studies with SMBG data to determine if the availability of SMBG data in addition to HbA1c values changed the primary care physicians' therapeutic recommendations. At the end of the study, a survey questionnaire evaluating the value of episodic SMBG data in addition to HbA1c results was administered.

In reviewing the case studies with SMBG data, 78% of the primary care physicians correctly identified normoglycemia, hypoglycemia, hyperglycemia, elevated fasting values and elevated postprandial values. When the primary care physicians assessed case studies with SMBG data, 77% of them changed the therapeutic decisions they had made previously when evaluating the case studies without SMBG data. When hypoglycemia was identified, primary care physicians decided to change the time the current medication was given, reduce the dose of the current medication, discontinue the medication altogether, or change to a new medication. When frequently elevated fasting levels or elevated postprandial SMBG levels were apparent, primary care physicians elected to change the time the current medication was given, increase the dose of the current medication, switch to a new medication, or add a new medication to the current treatment regime.

Primary care physicians were asked to assess the added value of SMBG data when presented with HbA1c data. Approximately 86% of the primary care physicians found the SMBG information to be of equal or greater value than the HbA1c while less than 14% found it to be of lesser or no value. This study shows that primary care physicians may correctly identify glycemic abnormalities in episodic, intensive SMBG data. Indeed, PCP's assessment of the SMBG data prompted most of them to change the therapeutic choices made initially when the case studies did not include the SMBG data. In addition, the vast majority of participating PCPs found the SMBG data to be valuable when evaluating the case studies.

The effectiveness of blood glucose and lifestyle factors tracking apparatus 100 on improving patient care was studied in a study presented at the American Diabetes Association in 2007 titled "Development of a Novel bG Analysis System for Episodic bG Monitoring in Persons with Type 2 Diabetes."

In the study, thirty subjects with type 2 diabetes used the blood glucose and lifestyle factors tracking apparatus 100 to determine if the subjects could use and learn from the system. The subjects were trained to use a blood glucose meter and the blood glucose and lifestyle factors tracking apparatus 100. On completion of the study, the blood glucose meters were downloaded, the blood glucose and lifestyle factors tracking apparatus 100 were collected, and the subjects completed a questionnaire. Table V represents the demographics of the subjects.

TABLE V

| Age (years) | Gender (M/F) | Duration of Diabetes (years) | A1c (%) | Self-reported bG tests/day | Self-reported bG tests/week |
|---|---|---|---|---|---|
| 66 +/− 9.6 | 15/15 | 9.6 +/− 6.3 | 8.0 +/− 2.1 | 1.8 +/− 0.9 | 6.1 +/− 1.5 |

After training and familiarization with blood glucose and lifestyle factors tracking apparatus 100, written blood glucose values in row 178 on the completed blood glucose and lifestyle factors tracking apparatus 100 matched meter downloads greater than 90% of the time. The subjects rated the following features of blood glucose and lifestyle factors tracking apparatus 100 identified in Table VI on a scale of 1 to 7 with 1 being the most positive response:

TABLE VI

| Easy to Complete | # of Test Days | # of Tests per Day | Presence of bG Targets | Presence of Too High/ Low Ranges |
|---|---|---|---|---|
| 1.6 +/− 0.9 | 1.6 +/− 0.9 | 3.6 +/− 2.0 | 1.4 +/− 0.8 | 1.5 +/− 0.9 |

Many of the subjects reported being genuinely surprised by their blood glucose readings and 68% of subjects made correlations between meal size and postprandial blood glucose values. Many of the subjects wanted to take their completed blood glucose and lifestyle factors tracking apparatus 100 to their physicians. More than 90% of the subjects said that despite the test frequency, they would be willing to use the blood glucose and lifestyle factors tracking apparatus 100 again every 3 months if asked to by their physicians. These findings indicate that persons with type 2 diabetes are willing to perform episodic blood glucose monitoring if their physicians ask them to, can learn from completing the blood glucose and lifestyle factors tracking apparatus 100, and might be more motivated to improve their diabetes self-care as a result.

Blood glucose and lifestyle factors tracking apparatus 100 may be implemented in a variety of implementation scenarios. A first scenario is in conjunction with a physician's office. The physician's office contacts the patient two weeks prior to the next scheduled office visit to remind the patient about the next appointment and to inform about important testing materials the physician wants the patient to complete beforehand and discuss at the next appointment. The physician's office mails the blood glucose and lifestyle factors tracking apparatus 100 to the patient together with a test strip prescription for test strips for a blood glucose meter. In one embodiment, the blood glucose and lifestyle factors tracking apparatus 100 is packaged with the test strips for the blood glucose meter and the physician simply provides a test strip prescription. The patient completes the blood glucose and lifestyle factors tracking apparatus 100 prior to the office visit and brings the completed blood glucose and lifestyle factors tracking apparatus 100 to the office visit. The physician and the patient discuss the completed blood glucose and lifestyle factors tracking apparatus 100 together and decide on potential therapy changes.

A second scenario is for emerging markets. In an emerging market, blood glucose meters are generally scarce and self-monitoring of blood glucose is rarely performed. Further, HbA1c testing is often not performed. A pool of blood glucose meters are provided to a care facility. An exemplary care facility is a regional hospital. A patient borrows a meter from the pool of meters provided to the regional hospital. The patient also receives a test strip prescription and the blood glucose and lifestyle factors tracking apparatus 100. In one embodiment, blood glucose and lifestyle factors tracking apparatus 100 is packaged with the test strips for the blood glucose meter and the physician simply provides a test strip prescription along with the meter from the pool of meters. The patient tests his/her blood glucose for three days and records the results along with the lifestyle factors with blood glucose and lifestyle factors tracking apparatus 100. The following week the patient returns the meter and the completed blood glucose and lifestyle factors tracking apparatus 100 to his/her physician in the regional hospital during an in-office consultation. The physician discusses the results with the patient, evaluates the current therapy, and makes suggestions for changes in therapy or lifestyle, if applicable. The meter is returned to the pool of meters after cleaning to prevent cross-contamination of blood.

A third scenario is for a care facility setting. A diabetes center in the care facility calls the patient prior to the next scheduled office visit to remind the patient about the next appointment and to let him/her know, that he/she will be receiving important testing materials to be completed and discussed at the appointment. In one embodiment, the patient is contacted about two weeks prior to the next scheduled office visit. The care facility mails or otherwise provides the blood glucose and lifestyle factors tracking apparatus 100 to the patient together with a test strip prescription. In one embodiment, blood glucose and lifestyle factors tracking apparatus 100 is packaged with the test strips for the blood glucose meter and the care facility simply provides a test strip prescription to the patient.

Figure 12:
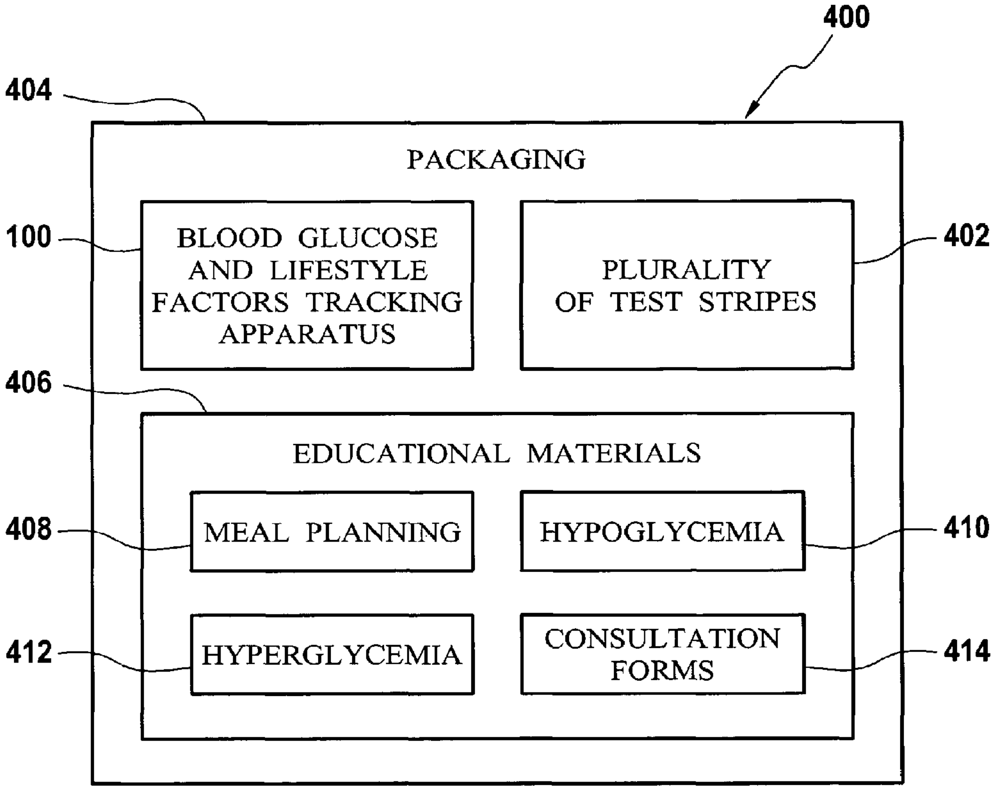
FIG. 12 is a representation of a kit including a blood glucose and lifestyle factors tracking apparatus.

Referring to FIG. 12, an exemplary kit 400 including a plurality of test strips 402 and blood glucose and lifestyle factors tracking apparatus 100 is represented. Both the plurality of test strips 402 and blood glucose and lifestyle factors tracking apparatus 100 are provided within packaging 404. In one embodiment, education information 406 is also provided in kit 400. Exemplary educational information 406 includes meal planning information 408, hypoglycemia information 410, hyperglycemia information 412, and consultation forms 414.

Returning to the third scenario, the patient tests for three days with the blood glucose and lifestyle factors tracking apparatus 100 and returns the completed blood glucose and lifestyle factors tracking apparatus 100 at his/her next appointment. The physician and the patient discuss results, evaluate the current therapy, and discuss changes to the therapy and/or lifestyle.

A fourth scenario is for pharmacists. The pharmacist gives the patient the blood glucose and lifestyle factors tracking apparatus 100 when buying a new meter and/or test strips. In one embodiment, blood glucose and lifestyle factors tracking apparatus 100 is packaged with the test strips for the blood glucose meter or with the meter. In one embodiment, blood glucose and lifestyle factors tracking apparatus 100 is provided as part of a kit 400 including one or more blood glucose and lifestyle factors tracking apparatus 100, educational sheets on hypoglycemia, hyperglycemia, and meal planning, and consultation forms. The patient is asked to complete the blood glucose and lifestyle factors tracking apparatus 100 and return the completed blood glucose and lifestyle factors tracking apparatus 100 to the pharmacist. In one embodiment, the pharmacist evaluates the effectiveness of the current therapy and counsels the patient on how he responds to food and medication and provides recommendations. The pharmacist may offer to share the evaluation with the patient's primary care physician. In one embodiment, pharmacists may receive reimbursement for counseling services.

This scenario has many benefits for the patient, the pharmacist, and the physician. Regarding benefits for the patient, the pharmacist trains the patient in the proper use of the meter. Further, the patient learns how diet affect their blood glucose values. Additionally, the patient gets used to using the blood glucose and lifestyle factors tracking apparatus 100 on a regular basis. Finally, the physician is likely to intensify therapy more quickly leading potentially to better outcomes for the patient. Regarding benefits for the pharmacist, the pharmacist provides greater value to the patient through training and analysis of therapy. The pharmacist has improved job satisfaction because they are more fully utilizing their training and education. Additionally, the customer relations with both patients and physicians to the pharmacist are likely strengthened. Regarding benefits for the physician, the physician gets a second opinion on the effectiveness of the patient's therapy and has appointments with patients to discuss the results. Further, the physician may use the information provided by the blood glucose and lifestyle factors tracking apparatus 100 to intensify therapy which will likely achieve better outcomes for the patient and may earn more from payers.

In one embodiment, a completed blood glucose and lifestyle factors tracking apparatus 100 is input to a computing device 300 to provide additional analysis of the data indicated on the completed blood glucose and lifestyle factors tracking apparatus 100 and/or to compare the data on the completed blood glucose and lifestyle factors tracking apparatus 100 to historical data for the patient. In one embodiment, the historical data is derived for prior instances of the completed blood glucose and lifestyle factors tracking apparatus 100.

Figure 10:
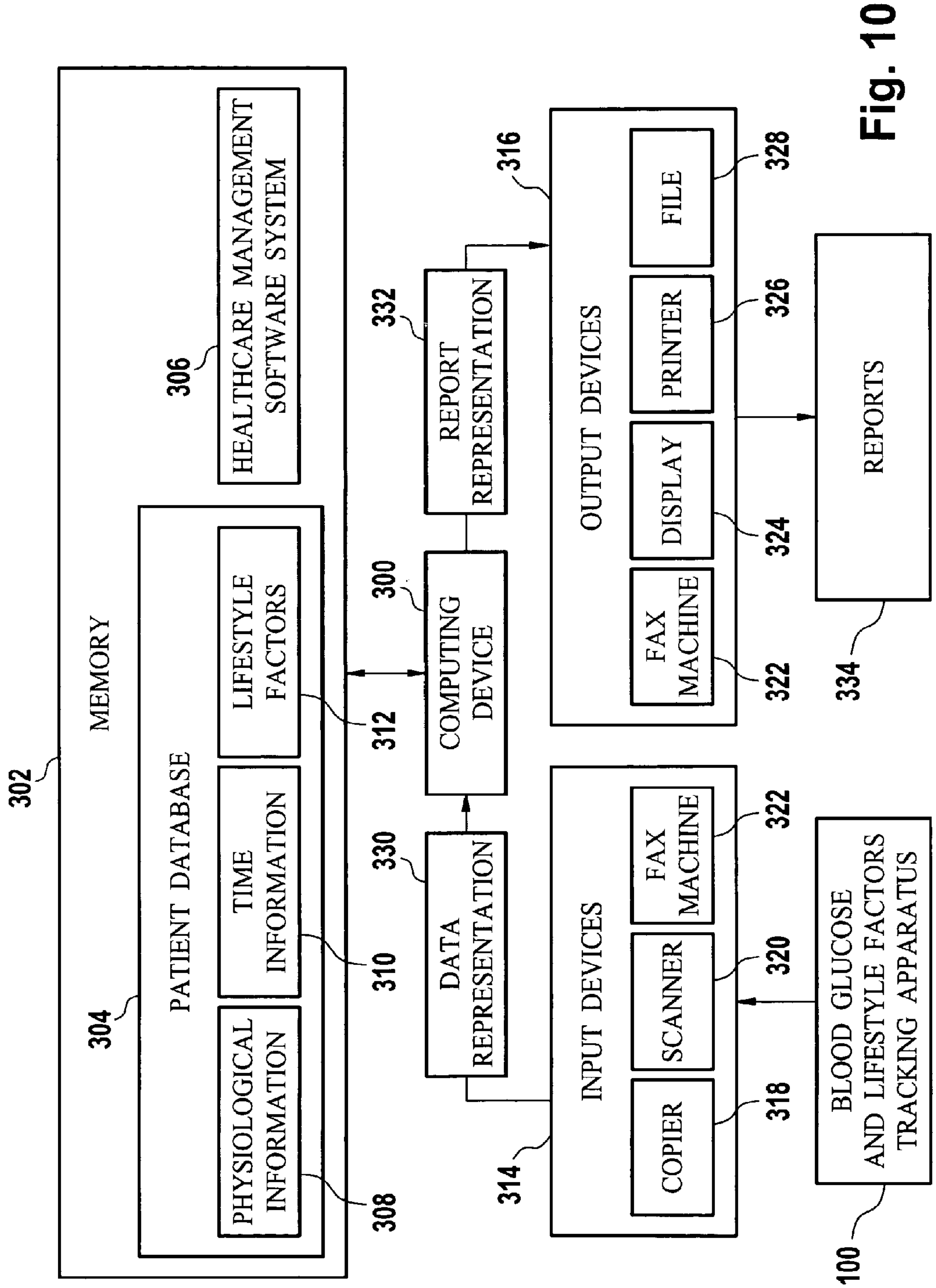
FIG. 10 is a representation of a system for analyzing the results of a completed blood glucose and lifestyle factors tracking apparatus.

Referring to FIG. 10, a computing device 300 is shown. Computing device 300 may be a general purpose computer or a portable computing device. Although computing device 300 is illustrated as a single computing device, it should be understood that multiple computing devices may be used together, such as over a network or other methods of transferring data. Exemplary computing devices include desktop computers, laptop computers, personal data assistants ("PDA"), such as BLACKBERRY brand devices, cellular devices, tablet computers, infusion pumps, blood glucose meters, or an integrated device including a glucose measurement engine and a PDA or cell phone.

Computing device 300 has access to a memory 302. Memory 302 is a computer readable medium and may be a single storage device or multiple storage devices, located either locally with computing device 300 or accessible across a network. Computer-readable media may be any available media that can be accessed by the computing device 300 and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store the desired information and which can be accessed by the computing device 300.

Memory 302 includes one or more patient databases 304 and healthcare management software system 306. Patient databases 304 include physiological information 308 related to one or more patients. Exemplary physiological information includes blood glucose values, HbA1c values, Albumin values, Albumin excretion values, body mass index values, blood pressure values, carbohydrate values, cholesterol values (total, HDL, LDL, ratio) creatinine values, fructosamine values, HbA1 values, height values, insulin dose values, insulin rate values, total daily insulin values, ketone values, microalbumin values, proteinuria values, heart rate values, temperature values, triglyceride values, and weight values. Physiological information 308 may be provided directly by the patient, provided by a caregiver, and/or provided by one or more sensors. Exemplary sensors are provided in insulin pumps and glucose meters. The physiological information 308 is related to time information 310 which corresponds to the time the measurement was taken or represents a period of time within which a measurement was taken. Patient databases 304 further include lifestyle factors information 312. Lifestyle factors information 312 is related to time information 310 and/or physiological information 308.

Computing device 300 has access to one or more input devices 314 and one or more output device 316. Exemplary input device 314 include a copier 318, a scanner 320, and a fax machine 322. The input device 314 is able to receive a completed blood glucose and lifestyle factors tracking apparatus 100 and provide an electronic representation of the data thereon. Exemplary output devices 112 include a fax machine 322, a display 324, a printer 326, and a file 328. File 328 may have various formats. In one embodiment, file 328 is a portable document format (PDF) file. In one embodiment, file 328 is formatted for display by an Internet browser, such as Internet Explorer available from Microsoft of Redmond, Wash., and may include one or more of HyperText Markup Language ("HTML"), or other formatting instructions. In one embodiment, file 328 is a file stored in memory 302 for transmission to another computing device and eventual presentation by another output device or to at least influence information provided by the another output device.

In one embodiment, the completed blood glucose and lifestyle factors tracking apparatus 100 is provided to an exemplary input device 314. The input device 314 provides an electronic representation 330 of the data provided on the completed blood glucose and lifestyle factors tracking apparatus 100. The electronic representation 330 is provided to computing device 300. Computing device 300 inputs the electronic representation 330 into patient database 304 through healthcare management software system 306. Computing device 300 then generates an electronic report 332 with healthcare management software system 306. The electronic report 332 is provided to output device 316. With output device 316, a user may produce a hard copy report 334.

Healthcare management software system 306 includes instructions which when executed by computing device 300 present physiological information 308 or information based on physiological information 308 to an output device 316. Exemplary information presented by healthcare management software system 306 to output device 316 include diaries of blood glucose values and reports showing a plurality of blood glucose values and the times or times blocks to which the blood glucose values correspond. Exemplary reports include standard day reports wherein the blood glucose values are grouped according to the time of day taken, standard week reports wherein the blood glucose values are grouped according to the day of the week taken, trend graphs to illustrate temporal trends in blood glucose values, and other suitable reports and/or graphs.

Figure 11:
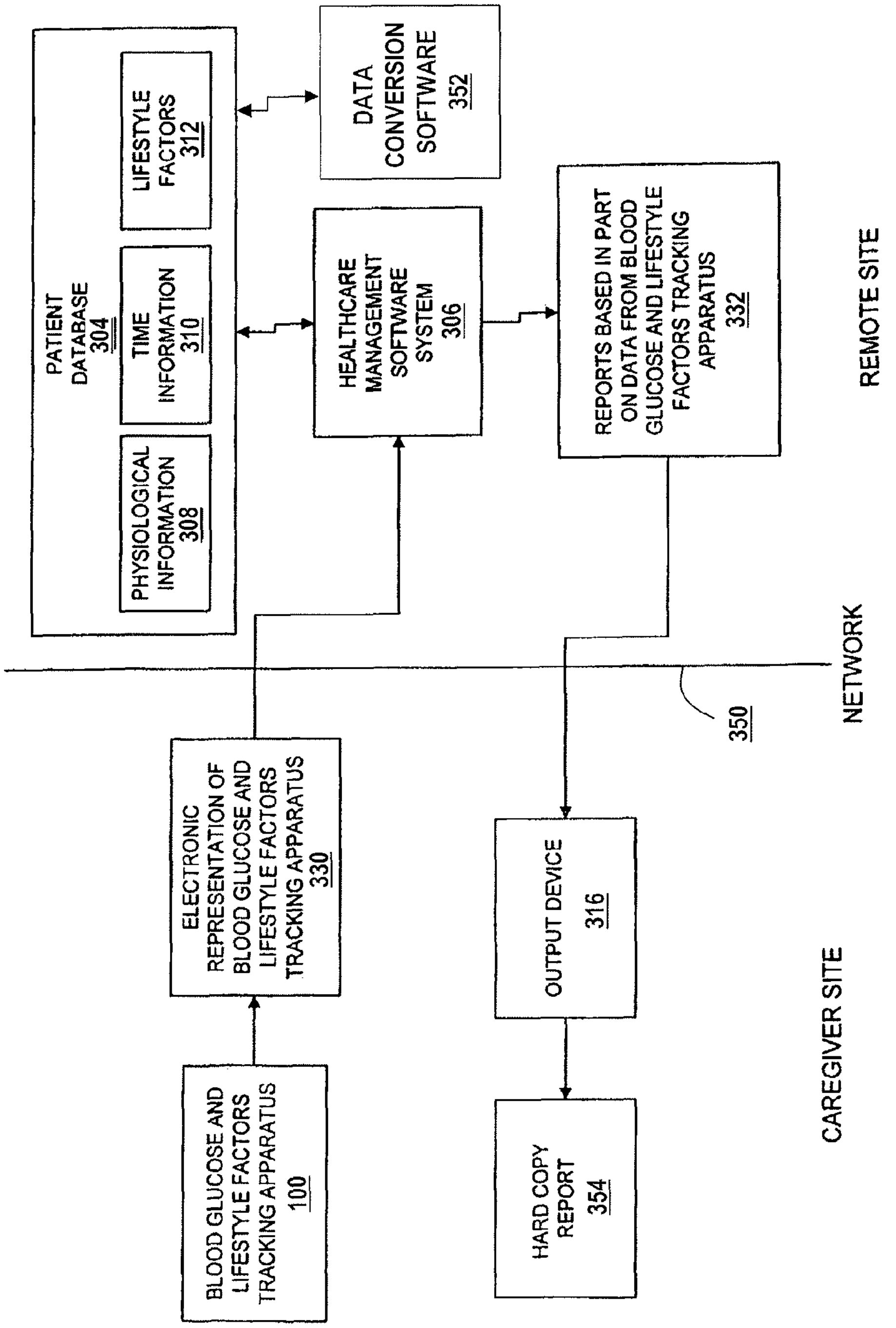
FIG. 11 is a representation of a method for analyzing the results of a completed blood glucose and lifestyle factors tracking apparatus.

Referring to FIG. 11, an exemplary representation of the processing of a completed blood glucose and lifestyle factors tracking apparatus 100 is shown. A completed blood glucose and lifestyle factors tracking apparatus 100 is taken by the patient to a caregiver site. An exemplary caregiver site is the patient's primary physician's office. The completed blood glucose and lifestyle factors tracking apparatus 100 is converted into an electronic representation 330 of the completed blood glucose and lifestyle factors tracking apparatus 100. In one embodiment, the electronic form of the completed blood glucose and lifestyle factors tracking apparatus 100 does not retain details regarding the appearance of the blood glucose and lifestyle factors tracking apparatus 100, but simply rather just a representation of the data provided on the completed blood glucose and lifestyle factors tracking apparatus 100.

The electronic representation 330 is transferred over a network 350 to a remote site. Exemplary networks include the internet, a phone network, a cellular network, a cable network, a local area network, a wide are network, and other suitable networks. At the remote site data conversion software 352 extracts the data provided in the completed blood glucose and lifestyle factors tracking apparatus 100 from electronic representation 330. In one embodiment, wherein a scanned view of completed blood glucose and lifestyle factors tracking apparatus 100 is provided to data conversion software 352, data conversion software 352 includes optical character recognition software to convert handwritten information into digital information.

The data derived from electronic representation 330 is stored in patient database 304. Healthcare management software system 306 generates one or more reports 332 including information derived from electronic representation 330. In one embodiment, electronic report 332 further includes historical data or other physiological information 308 provided in patient database 304. Exemplary reports may provide a mean glucose value, a percentage of blood glucose values in and out of range, trend analysis, and other suitable pieces of information.

Reports 332 are transferred back through network 350 to an output device 316 at the caregiver's site. At the caregiver's site a hard copy 354 of the report may be generated for the patient, for the caregiver, and/or for the patient file.

In one embodiment, computing device 300 includes software which based on the recorded blood glucose values, the time period of the blood glucose values (preprandial, postprandial, fasting), the recorded responses to the lifestyle factors, and/or additional information (medication information and insulin type and dosage) provides to the doctor at least one of an analysis of the patient's current therapy and one or more suggested changes to the current therapy, if any. For instance, based on the information related to George the software would recognize that the postprandial glucose values are consistently above goal and suggest that George consult with a dietitian to learn how food affects SMBG values, suggest adding an incretin agent, and/or suggest adding preprandial insulin.

Although the invention has been described in detail with reference to certain preferred embodiments, variations and modifications exist within the spirit and scope of the invention as described and defined in the following claims.

The invention claimed is:

1. A method of assessing blood glucose levels, comprising providing a patient with a blood glucose and lifestyle factors tracking apparatus, the blood glucose and lifestyle factors tracking apparatus comprises:
- a foldable substrate having
  - a front side including a plurality of regions for tracking blood glucose values;
  - a second side including a portion having a plurality of instructions for using the plurality of regions for tracking blood glucose values; and
  - a foldable portion,
  - wherein the plurality of instructions for using the plurality of regions for tracking blood glucose values are printed on the second side of the foldable substrate in a manner that folding the foldable portion causes the plurality of instructions on the second side to overlap the plurality of regions for tracking blood glucose values of the front side in a manner to instruct the patient to input blood glucose and lifestyle factors into the plurality of regions for tracking blood glucose values on the front side.

2. The method of claim 1 further comprising receiving the blood glucose and lifestyle factors tracking apparatus from the patient.

3. The method of claim 1 further comprising providing a prescription for test strips for a blood glucose meter to the patient.

4. A method of assessing blood glucose levels, comprising providing a patient with a blood glucose and lifestyle factors tracking apparatus, the blood glucose and lifestyle factors tracking apparatus comprises:
- a foldable substrate having:
  - a front side including a plurality of regions for tracking blood glucose values, the plurality of regions for tracking blood glucose values including a first region for manually recording an actual blood glucose value and a second region for placing a graphical marker indicating a selection in a first range of a plurality of ranges of blood glucose values;

a second side including a portion having a plurality of instructions for using the plurality of regions for tracking blood glucose values; and a foldable portion, wherein the plurality of instructions for using the plurality of regions for tracking blood glucose values are printed on the second side of the foldable substrate in a manner that folding the foldable portion causes the plurality of instructions on the second side to overlap the plurality of regions for tracking blood glucose values of the front side in a manner to instruct the patient to input blood glucose and lifestyle factors in the first region for manually recording an actual blood glucose value and the second region for placing a graphical marker on the front side.

5. The method of claim 4 further comprising receiving the blood glucose and lifestyle factors tracking apparatus from the patient.

6. The method of claim 4 further comprising providing a prescription for test strips for a blood glucose meter to the patient.

7. A method of assessing blood glucose levels, the method including:

providing a patient with a blood glucose and lifestyle factors tracking apparatus, the blood glucose and lifestyle factors tracking apparatus including:

a foldable substrate having:

a front side including:

a first region for recording blood glucose values for at least a first fasting time period, a first preprandial time period, and a first postprandial time period for multiple consecutive days;

a second region for graphically representing the blood glucose values recorded in the first region, the second region being placed so that a first graphical marker in the second region corresponding to a first blood glucose value in the first region are aligned, the first graphical marker indicating a selection of a first range of a plurality of ranges of blood glucose values, the plurality of ranges including at least one range below a target range, at least one target range, and at least one range above a target range; and a third region for recording at least one lifestyle factor for each blood glucose value, the third region being positioned above the first region; and a second side including a portion having a plurality of instructions for using the plurality of regions for tracking blood glucose values; and a foldable portion, wherein the plurality of instructions for using the plurality of regions for tracking blood glucose values are printed on the second side of the foldable substrate in a manner that folding the foldable portion causes the plurality of instructions on the second side to overlap a portion of the front side in a manner to instruct the patient to input blood glucose and lifestyle factors in the first region for manually recording an actual blood glucose value and in the second region for placing a graphical marker on the front side, receiving the blood glucose and lifestyle factors tracking apparatus from the patient, the blood glucose and lifestyle factors tracking apparatus including a plurality of manually recorded blood glucose values, a manually drawn graphical representation of the plurality of manually recorded blood glucose values; and a plurality of manually recorded indicia for the at least one lifestyle factor for each manually recorded blood glucose value.

8. The method of claim 7, wherein the second region includes a plurality of boxes each corresponding to the plurality of ranges of blood glucose values, the first graphical marker being placed in a first box of the plurality of boxes, the range of blood glucose values of the first box including the first blood glucose value.

9. The method of claim 7, wherein the second region is color-coded to indicate whether the first graphical marker corresponds to the at least one target range.

10. The method of claim 7, wherein the at least one target range includes a postprandial target range and a preprandial target range.

11. The method of claim 7, wherein the first region includes a first plurality of boxes for recording the blood glucose values, the first plurality of boxes positioned in a first row; the second region includes a plurality of columns, each column including a second plurality of boxes; and the third region includes a third plurality of boxes for recording the at least one lifestyle factor, the third plurality of boxes positioned in a second row.

12. A system which assesses blood glucose levels comprising:

a blood glucose and lifestyle factors tracking apparatus comprising:

a foldable substrate having:

a front side including a plurality of regions for tracking blood glucose values;

a second side including a portion having a plurality of instructions for using the plurality of regions for tracking blood glucose values; and a foldable portion, wherein the plurality of instructions for using the plurality of regions for tracking blood glucose values are printed on the second side of the foldable substrate in a manner that folding the foldable portion causes the plurality of instructions on the second side to overlap the plurality of regions for tracking blood glucose values of the front side in a manner to instruct the patient to input blood glucose and lifestyle factors into the plurality of regions for tracking blood glucose values on the front side, a memory having a patient database;

an input device configured to both receive a completed blood glucose and lifestyle factors tracking apparatus and provide an electronic representation of data from the completed blood glucose and lifestyle factors tracking apparatus; and a computing device configured to input the electronic representation of the data from the completed blood glucose and lifestyle factors tracking apparatus in the patient database.

13. The system of claim 12, wherein the input device is one of a copier, a scanner, and a facsimile machine.

14. The system of claim 12, wherein the computing device is further configured to generate at least one report based on the data from the completed blood glucose and lifestyle factors tracking apparatus.

15. The system of claim 14, wherein the computing device is configured to generate the at least one report via health management software.

16. The system of claim 14, wherein the computing device is further configured to transmit the at least one report over a network to a remote computing device.

17. The system of claim 12, wherein the computing device is further configured to provide the at least one report to an output device.

18. The system of claim 17, wherein the output device is one of a display, a printer, a facsimile machine and an electronic file in a memory.

19. The system of claim 12, wherein the patient database includes physiological information related to one or more patients, time information related to the physiological information, and lifestyle factors information related to at least one of the time information and the physiological information.

20. The system of claim 17, wherein the electronic file is provided in a portable document format or formatted for display in an internet browser.

21. A system which assesses blood glucose levels of a patient comprising:

a blood glucose and lifestyle factors tracking apparatus comprising:

a foldable substrate having:

a front side including a plurality of regions for tracking blood glucose values;

a second side including a portion having a plurality of instructions for using the plurality of regions for tracking blood glucose values; and a foldable portion, wherein the plurality of instructions for using the plurality of regions for tracking blood glucose values are printed on the second side of the foldable substrate in a manner that folding the foldable portion causes the plurality of instructions on the second side to overlap the plurality of regions for tracking blood glucose values of the front side in a manner to instruct the patient to input blood glucose and lifestyle factors into the plurality of regions for tracking blood glucose values on the front side;

a network;

a patient database; and a healthcare management software system configured to both receive via the network an electronic representation of the blood glucose and lifestyle factors tracking apparatus completed by the patient, and store data from the electronic representation of the completed blood glucose and lifestyle factors tracking apparatus in the patient database, wherein the plurality of regions for recording blood glucose values of the completed blood glucose and lifestyles tracking apparatus includes recorded blood glucose values.

22. The system of claim 21, wherein the plurality of regions on the first side of the blood glucose and lifestyles tracking apparatus further includes a second region for placing a graphical marker indicating a selection in a first range of a plurality of ranges of blood glucose values.

23. The system of claim 21, wherein the healthcare management software system is further configured to generate at least one report derived from the electronic representation of the completed blood glucose and lifestyle factors tracking apparatus.

24. The system of claim 21, wherein the network is selected from the internet, a phone network, a cellular network, a local area network, and a wide area network.

25. The system of claim 23, wherein the healthcare management software system is further configured to transfer the at least one report to an output device.

26. The system of claim 23, wherein the healthcare management software system is further configured to transfer the at least one report over the network to an output device.

27. The system of claim 23, wherein the at least one report includes historical data or physiological information related to one or more patients provided in the patient database.

28. The system of claim 23, wherein the at least one report is one of a mean glucose value, a percentage of blood glucose values in and out of a range, and trend analysis.

* * * * *